US006290713B1

(12) United States Patent
Russell

(10) Patent No.: US 6,290,713 B1
(45) Date of Patent: Sep. 18, 2001

(54) FLEXIBLE ILLUMINATORS FOR PHOTOTHERAPY

(76) Inventor: Thomas A. Russell, 7 Mustang Rd., Rancho Palos Verdes, CA (US) 90275

( * ) Notice: Subject to any disclaimer, the term of this patent is extended or adjusted under 35 U.S.C. 154(b) by 0 days.

(21) Appl. No.: 09/379,703

(22) Filed: Aug. 24, 1999

(51) Int. Cl.$^7$ ........................................ A61N 5/06
(52) U.S. Cl. ..................... 607/88; 607/89; 607/91
(58) Field of Search ................... 607/88, 89, 91; 606/2, 9, 13, 27, 10

(56) References Cited

U.S. PATENT DOCUMENTS

| D. 279,926 | 7/1985 | Rosenbaum . |
| 3,822,706 | 7/1974 | Simone et al. . |
| 3,877,437 | 4/1975 | Maintan et al. . |

(List continued on next page.)

FOREIGN PATENT DOCUMENTS

| 9700874 | 1/1997 | (WO) . |
| 9740888 | 6/1997 | (WO) . |
| 9700874 | 9/1997 | (WO) . |
| 9740888 | 11/1997 | (WO) . |
| 9856375 | 12/1998 | (WO) . |
| 9904628 | 2/1999 | (WO) . |
| 9920333 | 4/1999 | (WO) . |
| 9917668 | 5/1999 | (WO) . |
| 9922813 | 5/1999 | (WO) . |

OTHER PUBLICATIONS

Ennever et al, Society of Pediatric Research, May 1991, pp. 1–2.
Kang et al, Society for Pediatric Research, May 1992, pp. 1–4.
Hysmith et al, National Meeting of National Association of Neonatal Nurses, Sep. 1993. pp. 1–2.
George et al, Clinical Pediatrics, Apr. 1994, pp. 178–180.
Ohmeda Medical, Product Specifications Biliblanket Phototherapy System, Oct. 1995, pp. 1–2.
Dupont, Kapton Polyimide Film, No Date Given.
National Psoriasis Foundation, Overview of ultraviolet Light Therapy, pp. 1–3.
Rogers Corp., R/flex 2005 Flame Retardant Material System, No Date, pp. 1–4.
Patterson, Smartflex Systems, No Date Given, pp. 1–8.
Patterson, Electronic Packaging & Production, Jan. 1997, pp. 1–4.
Ohmeda Medical, Product Specifications Biliblanket Meter, Jan. 1997 pp. 1–2.
Ohmeda Medical, Biliblanket Plus Infant Phototherapy System, Date Unknown, pp. 1–5. Stearns, Printed Circuit Fabrication, vol. 21, Dec. 1998, No Date Given, pp. 42–44.
Southern Health Systems, Ohmeda Biliblanket v. Wallaby Phototherapy System for the Reduction of Bilirubin Levels in the Home Care Setting, Apr. 1993, pp. 1–2.

(List continued on next page.)

Primary Examiner—Roy Gibson
(74) Attorney, Agent, or Firm—Stout, Uxa, Buyan & Mullins; Frank J. Uxa

(57) ABSTRACT

Flexible illuminators for external phototherapy are disclosed each having at least one light generating source, preferably a plurality of light-generating sources, on a flexible substrate. The flexible substrate may be a circuit board, and the light-generating source may be surface mount LEDs. Structures for diffusing light emitted from the discrete light-generating sources and/or for transferring heat away from a skin contact surface are provided. The illuminators may be formed so as to be wrapped around an infant or a limb of an adult, or may be provided in larger configurations, such as a mat. The illuminators may be passively or actively cooled so that the skin contact surface remains below a desired temperature.

54 Claims, 16 Drawing Sheets

U.S. PATENT DOCUMENTS

| | | |
|---|---|---|
| 3,910,261 | 10/1975 | Ragsdale . |
| 4,155,358 | 5/1979 | McAllister et al. . |
| 4,220,162 | 9/1980 | Clark et al. . |
| 4,234,907 | 11/1980 | Daniel . |
| 4,248,245 | 2/1981 | Kempin . |
| 4,293,189 | 10/1981 | Morikawa . |
| 4,485,822 | 12/1984 | O'Connor et al. . |
| 4,560,883 | 12/1985 | Kerschgens . |
| 4,693,556 | 9/1987 | McCaughan, Jr. . |
| 4,754,372 | 6/1988 | Harrison . |
| 4,761,047 | 8/1988 | Mori . |
| 4,777,963 | 10/1988 | McKenna . |
| 4,822,335 | 4/1989 | Kawai et al. . |
| 4,831,024 | 5/1989 | Vreman et al. . |
| 4,907,132 | 3/1990 | Parker . |
| 4,911,166 | 3/1990 | Leighton et al. . |
| 5,005,108 | 4/1991 | Pristash et al. . |
| 5,069,220 | 12/1991 | Casparie et al. . |
| 5,069,222 | 12/1991 | McDonald, Jr. . |
| 5,074,632 | 12/1991 | Potter . |
| 5,136,480 | 8/1992 | Pristash et al. . |
| 5,140,027 | 8/1992 | Ong et al. . |
| 5,140,220 | 8/1992 | Hasegawa . |
| 5,169,395 | 12/1992 | Narciso, Jr. . |
| 5,196,005 | 3/1993 | Doiron et al. . |
| 5,219,346 | 6/1993 | Wagnieres et al. . |
| 5,231,684 | 7/1993 | Narciso, Jr. et al. . |
| 5,259,380 | 11/1993 | Mendes et al. . |
| 5,278,432 | 1/1994 | Ignatius et al. . |
| 5,293,875 | 3/1994 | Stone . |
| 5,301,090 | 4/1994 | Hed . |
| 5,339,223 | 8/1994 | Kremenchugsky et al. . |
| 5,363,458 | 11/1994 | Pan et al. . |
| 5,383,469 | 1/1995 | Vreman et al. . |
| 5,400,425 | 3/1995 | Nicholas et al. . |
| 5,426,635 | 6/1995 | Mitra et al. . |
| 5,445,608 | 8/1995 | Chen et al. . |
| 5,454,794 | 10/1995 | Narciso et al. . |
| 5,500,009 | 3/1996 | Mendes et al. . |
| 5,505,726 | 4/1996 | Meserol . |
| 5,536,265 | 7/1996 | Van Den Bergh et al. . |
| 5,549,660 | 8/1996 | Mendes et al. . |
| 5,591,219 | 1/1997 | Dungan . |
| 5,613,751 | 3/1997 | Parker et al. . |
| 5,616,140 * | 4/1997 | Prescott .................................. 606/10 |
| 5,618,096 | 4/1997 | Parker et al. . |
| 5,634,711 | 6/1997 | Kennedy et al. . |
| 5,695,583 | 12/1997 | Van Den Bergh et al. . |
| 5,698,866 | 12/1997 | Doiron et al. . |
| 5,728,090 | 3/1998 | Martin et al. . |
| 5,762,867 | 6/1998 | D'Silva . |
| 5,792,214 | 8/1998 | Larsson et al. . |
| 5,800,478 | 9/1998 | Chen et al. . |
| 5,800,479 | 9/1998 | Thiberg . |
| 5,824,023 | 10/1998 | Anderson . |
| 5,824,024 | 10/1998 | Dial . |
| 5,830,211 | 11/1998 | Santana et al. . |
| 5,835,648 | 11/1998 | Narciso, Jr. et al. . |
| 5,849,027 | 12/1998 | Gart et al. . |
| 5,857,761 | 1/1999 | Abe et al. . |
| 5,865,529 | 2/1999 | Yan . |
| 5,876,107 | 3/1999 | Parker et al. . |
| 5,876,427 | 3/1999 | Chen et al. . |
| 5,892,261 | 4/1999 | Lin et al. . |
| 5,908,415 | 6/1999 | Sinofsky . |
| 5,913,883 | 5/1999 | Alexander et al. . |
| 5,919,217 | 7/1999 | Hughes . |
| 5,921,652 | 7/1999 | Parker et al. . |
| 5,944,748 * | 8/1999 | Mager et al. ........................... 607/88 |
| 5,957,960 * | 9/1999 | Chen et al. ............................ 607/92 |
| 6,045,575 * | 4/2000 | Rosen et al. ........................... 607/88 |
| 6,063,108 * | 5/2000 | Salansky et al. ...................... 607/89 |
| 6,096,066 * | 8/2000 | Chen et al. ............................ 607/88 |

OTHER PUBLICATIONS

Hysmith et al, Ohmeda Biliblanket Phototherapy System v. Conventional Fluourescent Lights for the Treatment of Neonatal Jaundice in the Home, Apr. 1993, pp. 1–8.

Respironics, The Wallaby Fiberoptic Phototherapy Spotlight, No Date Given, pp. 1–25.

Schwoebel et al, Hyperbilirubinemia: New Approaches . . . , 1997.

Torres–Torres et al, The Mount Sanai Journal of Medicine, vol. 61, Oct. 1994, pp. 424–428.

Ennever et al. Abstract, Bright Light . . . , May 1991.

American Academy of Pediatrics, Pediatrics, vol. 94, Oct. 1994, pp. 1–18.

Minco Products, Inc. , Flex–Circuit Design Guide, 1997, pp. 1–28.

Minco Products, Inc., Flex Circuits, Bulletin FC–301, Sep. 1998, pp. 1–8.

McGoldrick, Electronic Design, Dec. 1996, pp. 68–69.

Dept. of Neonatal Medicine Nursing Protocols, Phototherapy, 1998, pp. 1–7.

Patterson, Flexible Circuits Engineering, Aug. 1996, pp. 1–2.

Nichia Chemical Industries, Specifications for Nichia Chip Type Blue LED, 1998, pp. 1–8.

Philips, Special Blue Fluorescent Lamps Product Bulletin, No Date, pp. 1 & 3.

Ohmeda medical, Biliblanket Plus Phototherapy System, Oct. 1998, pp. 1–4.

Smartflex Systems, Chip–On Flex Design Guidelines, No Date Given, pp. 1–2.

Dupont, CB Series Polymer Thick Film Pastes, No Date Given, pp. 1–4.

Ennever, Clinics in Perinatology, vol. 17, Jun. 1990, pp. 467–481.

Vreman et al, Pediatric Research, vol. 44, 1998, pp. 804–809.

Roberts et al, Technoly Focus, pp. 1–4, Feb. 1992.

* cited by examiner

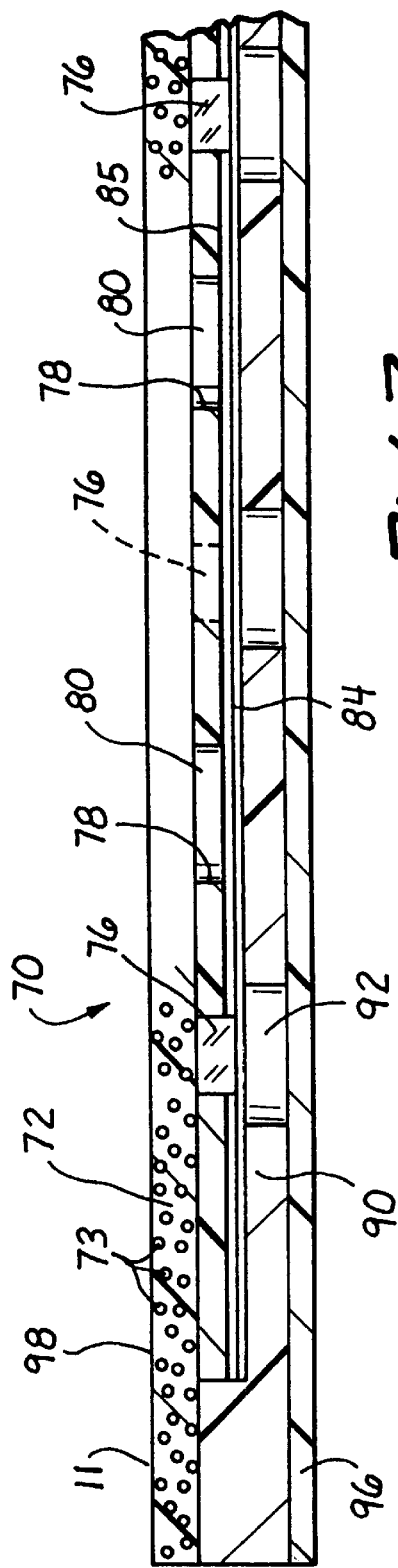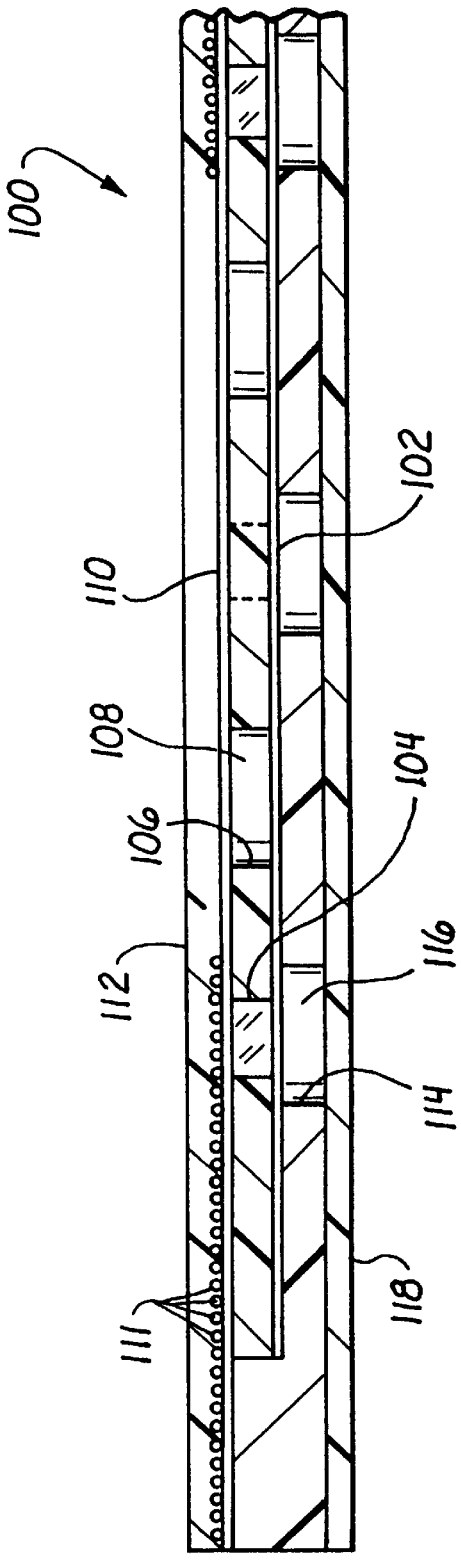

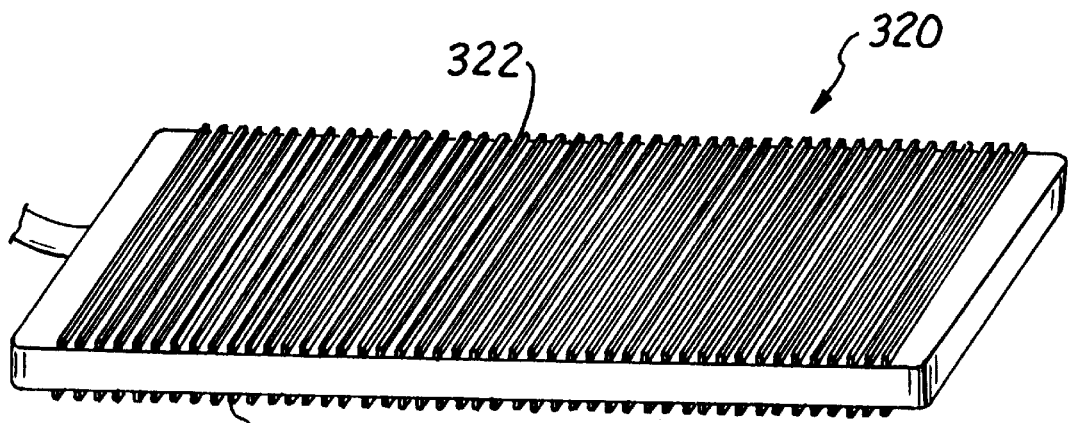
Fig. 15A
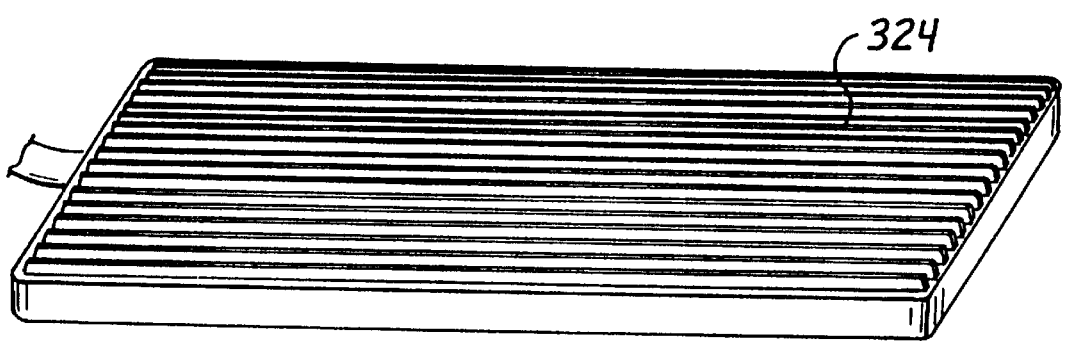
Fig. 15B
Fig. 15C
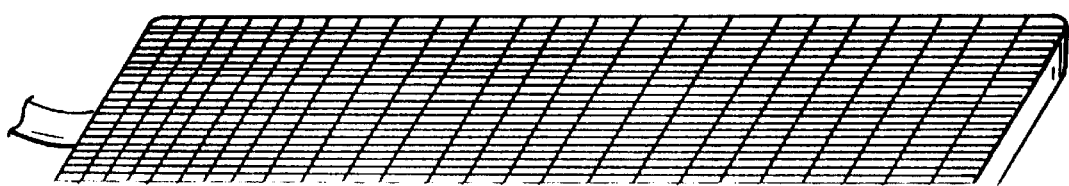

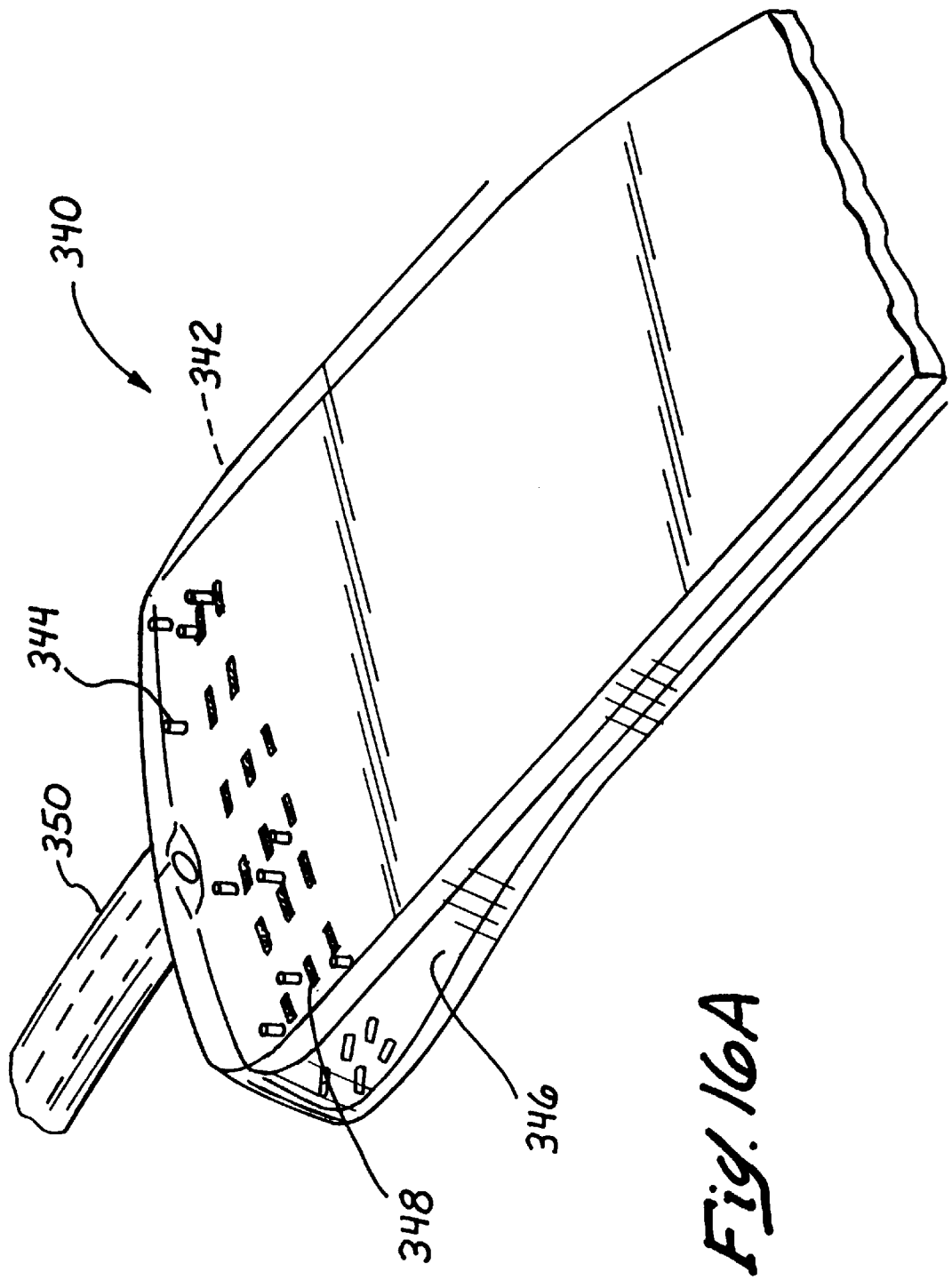

FLEXIBLE ILLUMINATORS FOR PHOTOTHERAPY

FIELD OF THE INVENTION

The present invention pertains to devices and methods of external phototherapy and, in particular, to phototherapy devices for use in close proximity or in contact with the skin of the patient. More specifically, the present invention provides a flexible, high-intensity flexible phototherapy device that can be safely and comfortably used.

BACKGROUND OF THE INVENTION

The term "phototherapy" relates to the therapeutic use of light, and the term "illuminator" refers to a device that is intended to be used externally to administer light to the skin for therapeutic purposes. Some phototherapy devices, in contrast, are provided on probes and are designed to be used internally.

External phototherapy has been shown effective in treating various medical conditions. For example, studies have shown that certain light spectra are effective in treating bulimia nervosa, herpes, psoriasis, seasonal affective disorder, sleep disorders, acne, skin cancer, and other conditions. One of the conditions most widely treated with phototherapy is hyperbilirubinemia in newborn infants, typified by an elevated level of a toxic molecule known as bilirubin in the infant's blood. During a natural process where the body scavenges iron from a substance known as "heme," bilirubin is produced. Normally, bilirubin is a conjugated within the liver and excreted. A fetus cannot conjugate bilirubin, however, so it is cleared via the placenta. During the initial neonatal period, the infant's liver may be too immature to conjugate bilirubin. If the condition remains untreated, the serum bilirubin levels may increase to the clinical condition of jaundice, since there is no effective excretory pathway. High levels of bilirubin in the neonate may cause irreversible brain damage and even death.

About 60 percent of newborns become clinically jaundiced at some time during the first week after birth. The proportion increases to 80 percent in premature infants. Consequently, hyperbilirubinemia is one of leading causes of hospital readmissions of newborns. Phototherapy is the treatment of choice for neonatal unconjugated hyperbilirubinemia, and has been used worldwide for decades with no known significant side effects. Phototherapy treats hyperbilirubinemia by changing bilirubin from its non-water-soluble form to water-soluble byproducts which can be bound to albumin, transported to the liver, and excreted.

As a yellowish pigment, bilirubin absorbs visible light in the blue, violet, and green spectra, and most readily absorbs wavelengths in the range of 400–500 nm, with a maximum absorption peak in the 450–460 nm range, i.e., blue light. Green light is also effective in phototherapy because light of longer wavelengths penetrates the skin more deeply. There is a dose-response relationship in the efficacy of phototherapy. That is, there is an increased response for higher doses of therapeutic light, as shown by a decrease in bilirubin levels.

Illuminators for phototherapy which are known in the art fall into two general categories: banks of light and fiber-optic illuminators. The earliest phototherapy illuminators included banks of light placed over an incubator, above an open bassinet, under a hood, or under a transparent support. Either fluorescent tubes or metal halide lamps typically serve as the light sources, although arrays of light-emitting diodes (LEDs) are also known in the art. These light sources are spaced from the infant and illuminate the whole body of the infant.

Illuminators using banks of light suffer from a number of drawbacks. The infant must wear sometimes uncomfortable eye protection during this treatment, either by using an appropriate shield or goggles, or even by taping the eyes shut, because the intense light can cause permanent eye damage. The relatively large size of the equipment takes up valuable free space in a typically cramped neonatal hospital ward. The banks of lights generate undesirable heat, and interfere with personnel attending to the patient. The heat generated is of vital concern in infant phototherapy. Newborn infants are extremely sensitive to heat, and it has been found that the heart rate of preterm infants increases significantly when the environmental temperature is raised as little as five degrees Celsius above normothermia. Hyperthermia has been associated with heart irregularities, heatstroke, and sudden infant death syndrome. Consequently, the infant's temperature must be frequently monitored when the infant is under a bank of phototherapy lights. Moreover, the relatively bulky equipment is not well-suited for home use, and thus the newborn infant must remain longer in the hospital.

Primarily in response to the desire of parents to bring their newborn infants home sooner, portable fiber-optic mats or wraps have been developed. These fiber-optic illuminators transmit light from a remote source through a fiber-optic cable to a flexible mat having a weave or other arrangement of optical fibers which can be worn next to the patient's skin. Because fiber-optic illuminators are placed around or under only a portion of the infant, its eyes are not exposed to intense light and eye protection is not necessary. Because the light source is remote from the flexible mat next to the patient, a filter can be used to attenuate any appreciable heating. Most importantly, since infant can be held and attended to while undergoing phototherapy treatment, fiber-optic illuminators promote better infant-parent bonding during the first few weeks of life. Commercial fiber-optic phototherapy illuminators include Ohmeda's BiliBlanket and Respironics'Wallaby II, which have tungsten halogen lamps and quartz halogen lamps, respectively, as their light sources.

FIG. 1 illustrates a fiber-optic mat type of illuminator of the prior art. The illuminator includes a woven fiber-optic mat 10 connected by a cable 12 to a housing 14 for a source of light. Alternatively, the mat may contain a plurality of fiber-optic strands which are cut or otherwise adapted to distribute light in a pinpoint pattern over the surface of the mat. The connector 16 is affixed to an end of the cable 12 and is inserted into the housing 14 to receive the light energy. The housing 14 includes the front face 24 on which may be mounted a power switch 20, a control indicator 22, and indicator lights 26 and 28. The mat 10 comprises a plurality of optical fibers woven so as to emit light energy for phototherapy.

Despite several advantages over radiant-type illuminators, fiber-optic illuminators are not ideal for several reasons. Significantly, fiber-optic illuminators typically deliver a lower overall amount of light than overhead banks of light, because the light is transmitted from a remote source to a relatively small fiber-optic mat. Moreover, to deliver even this limited amount of light, fiber-optic illuminators require a high-intensity light source such as halogen lamp, and an expensive optical filter to eliminate unwanted heat and ultraviolet light. Woven fiber-optic mats typically rely upon the geometry of the various emitting layers of fiber to control the level of light emittance. Since the patient is in direct contact with the fiber-optic mat, there is some pressure applied which may change the geometry, and thus change the level of light. In contrast, fiber-optic mats using a plurality of cut strands to distribute light are often thicker near the light source where the strands originate than at the other end of the mat. In either case, the light intensity may be more concentrated near the light source than at the other end of the mat.

Recently, researchers at Stanford University have studied the efficacy of high-intensity light-emitting diodes (LEDs) for phototherapy of hyperbilirubinemic neonates. The in vitro photodegradation of bilirubin in human serum albumin from both LEDs and conventional light sources was measured, with the conclusion that LEDs are more effective. The use of LEDs for use in home phototherapy devices was mentioned. However, no specific device structure was disclosed, nor was any consideration given for the safety and comfort of the patient, for example a newborn infant, undergoing phototherapy.

Several hurdles remain to the use of LEDs in home phototherapy devices. Problems related to patient safety and comfort, as well as therapeutic effectiveness, must be solved before LEDs can by used in illuminators intended to be placed against the skin of a patient. Novel means of utilizing LEDs and similar intense light sources must be found before phototherapy safely effectively can be conducted at close range using such light sources for illumination. Such means must not materially increase the thickness, weight, or rigidity of a flexible illuminator, and must control heat and light output as necessary. There remains a need for a phototherapy illuminator which delivers a higher intensity of therapeutic light than current fiber-optic illuminators, while retaining the advantages of a flexible light-emitting mat and being safe and comfortable in use. These and other needs are met by the present invention, as is more fully discussed below.

SUMMARY OF THE INVENTION

The present invention provides a safe and effective phototherapy illuminator that can be positioned in close proximity to, or in direct contact with, the skin of a patient. The illuminator has a substrate having at least one light-generating source, preferably a plurality of such sources, thereon. The illuminator preferably includes a system for transferring heat generated by light-generating source away from the surface of the illuminator that faces or contacts the patient's skin. In this manner, the illuminator can be comfortably and safely used for extended periods, even for treating a neonatal patient. The heat transfer system may include passive and/or active cooling means. The illuminator preferably includes a system for diffusing the light emitted from the light-generating source(s) to help reduce any negative effects associated with excessive, inadequate, or uneven light intensity. The substrate is desirably flexible and the illuminator may be provided in a variety of body-conforming shapes to enable convenient treatment of different localized areas. When placed against the body of a patient, the illuminator leaves substantially no room for the light to escape. The reflecting means continue to reflect light reflected by the patient's tissue back to the patient until it is absorbed, and does so at close distance, maintaining light intensity. In short, the present invention provides a safe, effective and highly comfortable phototherapy illuminator that is currently unavailable to patients in need of such an illuminator.

Illuminator of the present invention are designed to prevent the significant amount of heat which LEDs generate from harming the patient, especially where arrays of LEDs are incorporated into a flexible wrap or mat. Indeed, traditional fan cooling is ineffective, since the wrap or mat is placed against the skin of the patient while in use. This leaves no room for air circulation and traps heat against the patient. The present invention, on the other hand, provides internal passive or active cooling of the illuminator.

In addition, the present invention includes means to prevent the loss of therapeutic light resulting from the reflective characteristic of the patient's skin. At present, no known phototherapy illuminator substantially prevents the loss of light reflected by the skin. The present invention repeatedly reflects the light that does not initially absorb into the skin of the patient back to the patient for as many times as necessary to ultimately cause absorption.

Furthermore, the present invention includes means designed to prevent the over-and under-exposure of the patient to therapeutic light. For various practical considerations, LED arrays often have unlighted gaps whose darkness highly contrast at close range with the intense light of adjacent LEDs. The present invention provides diffusing means to render the emitted light more uniform.

In accordance with one aspect of the present invention, an illuminator for delivering light energy to the skin for phototherapy is disclosed. The illuminator comprises a thin, lightweight flexible substrate having a plurality of conductive traces affixed thereto adapted to connect to an electrical power source. At least one discrete light generating source, preferably a plurality of discrete light-generating sources, are disposed on the substrate and are coupled to the conductive traces. Additionally, a covering at least partly surrounds the substrate and has an exterior surface that is spaced apart from the light-generating sources, the exterior surface being adapted to contact the skin of patient. Desirably, the illuminator is sufficiently lightweight and flexible to be worn against the skin of a newborn infant with injury. The illuminator preferably includes a light diffuser to render the light energy from the discrete light-generating sources more uniform. Additionally, a cooling means is desirably provided to maintain the exterior surface below a predetermined temperature.

In another embodiment, the present invention provides an illuminator for delivering light energy to the skin for phototherapy, comprising a thin, lightweight substrate, a plurality of conductive traces affixed to the substrate and adapted to connect to an electrical power source, at least one light-generating source disposed on the substrate and coupled to the conductive traces, and an interface at least partly covering or adjacent to the light-generating source on the substrate.

As used herein, the term "interface" refers to a region of the present illuminator located at least partially around and/or at least partially adjacent to a light generating source or sources of the illuminator. The interface can include a hollow or open space or a passage. The interface advantageously provides or is adapted to carry an effective heat transfer means or medium to dissipate heat generated by the light-generating source so that the illuminator can safely contact the skin of the patient. In one useful embodiment, the illuminator includes a covering and the interface provides or is adapted to carry a cooling means or medium between the covering and the substrate. For example, the interface may define spaces between the covering and a substrate for passive or active heat transfer. The illuminator may comprise a flexible mat connected to one or more conduits carrying electrical wires and the cooling fluid medium.

In a still further embodiment, an illuminator of the present invention for delivering light energy to the skin for phototherapy comprises a thin, lightweight substrate and a plurality of conductive traces affixed to the substrate adapted to connect to electrical power source. At least one discrete light-generating source, preferably a plurality of discrete light-generating sources are disposed on the substrate and are coupled to the conductive traces. An interface at least partly covers the light-generating sources on the substrate, and is effective to diffuse light emitted from the discrete light-generating source or sources. The illuminator is adapted to contact the skin of the patient. The interface may include any suitable light diffuser or diffusers. For example, light scattering elements, such as glass bubbles or hollow glass beads, and the like may be employed such as by suspension in a transparent or at least translucent matrix (e.g., silicone). Other light scattering elements include, but are not limited to, grains or particles of titanium oxide, titanium dioxide, zirconium oxide, zinc oxide, quartz, aluminum oxide, diamond dust, calcium carbonate, calcium fluoride, flint glass, barum-fluoride, other glasses, material which has a refractive index different, e.g., by at least about 5%, from the refractive index of the matrix in which the light scattering elements are placed, and the like and mixtures thereof. Alternatively, or in addition, the interface may have an exterior surface adapted to contact the skin of a patient, the exterior surface being irregular or uneven, preferably a matte finish, to defuse the light emitted from the discrete light-generating source or sources. For example, the interface may include indentations, texturing and the like surface features to diffuse the light.

A reflector or reflectors may also be employed to diffuse light. Also a Lambertian (random) reflecting surface or surfaces, for example, a white surface or surfaces, may be employed to diffuse light. Of course, combination of two or more light diffusers can be employed.

In one embodiment of the invention, in order to change the angle at which light from a light source encounters a different medium, and thereby increase internal reflection and diffusion, light refractive means, such as surface features, may be formed on or in the covering of the illuminator, or on or in the surface of an internal cavity in the illuminator. Alternatively, or in addition, in order to reflect a desired amount light away for the patient and towards the interface or substrate before it is emitted by the illuminator and reaches the patient, light reflecting means such as reflective coatings, inks, paints, or other materials, may be disposed on or in the covering, or on or in the surface of an internal cavity. Furthermore, light reflecting or refracting means, such as glass bubbles, titanium, metals, or the like, may be embedded in the interface in a desired configuration or quantity so as to diffuse light. Alternatively, or in conjunction with the foregoing, light reflecting or refracting means, preferably a Lambertian reflector, may be disposed on or in all or part of the substrate, to redirect light toward the patient or another diffusing means of the illuminator. The light refracting or reflecting means on or in the covering, the interface, and the substrate (each means constituting a "diffusing element"), may be adapted individually, or in various combinations or configurations, to diffuse light generated by the illuminator.

In a further embodiment the invention comprises a combination of two or more diffusing elements which are adapted to work together to diffuse light generated by the illuminator. Similarly, the invention may comprise a combination of three or more diffusing elements which are adapted to work together to diffuse light generated by the illuminator.

In a further aspect of present invention, a wearable phototherapeutic illuminator for delivering light energy to the skin comprises a flexible substrate and a least one light-generating source disposed on the substrate. A flexible, polymer layer covers the light-generating source, the layer permitting light energy to penetrate therethrough and being adapted to substantially conform, or structured to be capable of substantially conforming, to a portion of the skin of the patient. The layer is desirably a material chosen from the group consisting of silicone, urethane, and polyurethane, preferably transparent or translucent silicone. There may be a plurality of the light-generating sources, and a plurality of glass bubbles, or a blend of materials having different refractive indexes, may be dispersed throughout the layer to diffuse the light emitted from the light-generating sources. Reflective or refractive materials may be disposed on or in the cover to redirect light away from a particular location on the patient.

The invention also provides methods of phototherapy using the illuminator disclosed herein. The methods involve providing the illuminator having diffusive and/or cooling properties and applying the illuminator to the skin of the patient. Light energy is then provided to the patient sufficient to treat various disorders, including bulimia nervosa, herpes, psoriasis, seasonal affective disorder, sleep disorders, acne, skin cancer, and hyperbilirubinemia. The illuminator may be used in conjunction with photoreactive agents in photodynamic therapy.

Preferably, the average irradiance at the light emitting or contact surface of the present illuminator is more than about 50 microwatts per square centimeter.

Each of the features disclosed herein is included within the scope of the present invention. In addition, all combination of two or more of the presently disclosed features which are not mutually inconsistent or incompatible are also included within the scope of the present invention.

These and other aspect and advantages of the present invention are apparent in the following detailed description and claims, particularly when considered in conjunction with the accompanying drawings in which like parts bear like reference numerals.

BRIEF DESCRIPTION OF THE DRAWINGS

FIG. 7 is a sectional view through a portion of the illuminator of FIG. 6;

FIG. 8 is a sectional view through a portion of an alternative illuminator similar to that shown in FIG. 6;

FIGS. 15A–15C are perspective views of illuminators of the present invention having external cooling fins formed thereon;

FIG. 16A is a perspective view of an alternative illuminator having internal spacer pins;

DESCRIPTION OF THE PREFERRED EMBODIMENTS

Figure 1:
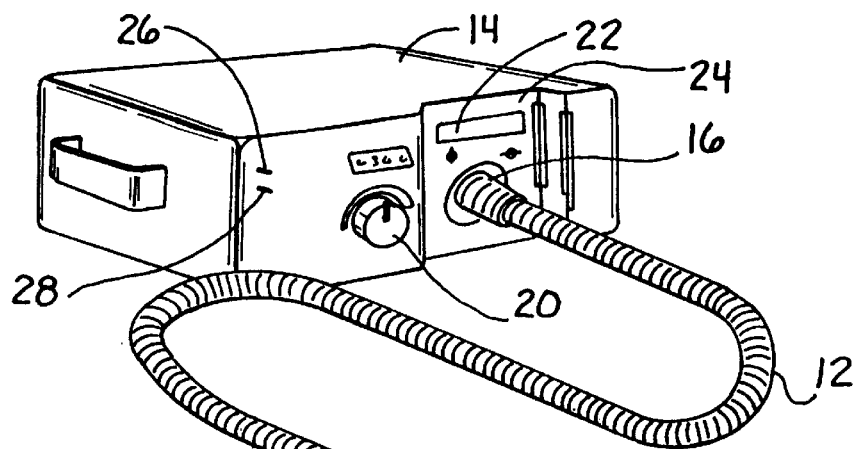
FIG. 1 is a perspective view of a prior art fiber-optic illuminator.

The present invention provides a flexible illuminator having a variety of applications, such as for the treatment of hyperbilirubinemia in neonates, and psoriasis, seasonal affective disorder, sleep disorders, herpes, acne, skin cancer, and other medical conditions. The invention is an advance over current fiber-optic type illuminators because of the increased intensity of the light-generating sources. Various configurations are described herein, none of which should be construed as particularly preferred in general. Instead, each configuration may be preferred in certain application over others.

In general, the present invention provides a phototherapy device comprising a substrate with at least one light-generating source thereon, and an interface between the substrate and the patient defining a contact surface adapted to be positioned in close proximity to, or in direct contact with, the skin of a patient. The various attributes of the phototherapy device will now be described, followed by a more detailed description of a number of exemplary embodiments. The phototherapy device is termed an "illuminator" herein.

The illuminator has a substrate having at least one electrically-powered light-generating source thereon. In this regard, the substrate may be variety of forms, typically including an insulating body on or in which a plurality of conductive leads or traces are provided. The light-generating source is mounted to the insulating body in electrical communication with the conductive traces. The preferred embodiment is a flexible substrate, as described below, but in some applications a rigid substrate may be suitable.

The present invention desirably utilizes any type of flexible substrate circuitry known in the arts. Typically, the term "flexible substrate" pertains to polymeric sheets which may be bent or rolled without breaking. In one embodiment, the substrate may be said to be flexible if it can be rolled, without breaking, into a cylindrical tube having a diameter less than 30 cm, and more preferably less than 5 cm. Examples of such flexible substrates are flexible printed circuitry laminates, which are composite of metal conductors and dielectric substrates bonded together by an adhesive system. Other flexible substrates may not use adhesive, such as copper foil which is electrolytically deposited or rolled-annealed. The substrates should be flexible and capable of withstanding the heat generated during the manufacturing process and by the light-generating sources. Consideration should also be given to the dimensional stability, chemical resistance, electrical properties, flame retardancy, and cost. Substrate can be either thermosetting or thermoplastic polymers, such as polyester and polyamide films. DuPont Kapton® and similar films are often preferred.

The flexible substrate may comprise a reflector on the side facing the contact surface for directing light from the light-generating sources toward the contact surface. The reflector may be a thin, flexible sheet adhered to the flexible substrate. Alternatively, the reflector may be comprised of reflective materials coated directly on the flexible substrate, or the substrate material itself may have reflective characteristics. The reflector is desirably perforated in the locations of the light-generating sources and may be coated to reflect an appropriate wavelength or range of wavelengths of light. The reflective materials may be metals such as aluminum, silver or gold (or alloys thereof), or dielectrics coated at thickness designed to reflect desired wavelengths, or reflective paint. In one embodiment, the reflector provides Lambertian reflectance and, for example, reflects and diffuses light by using a paint or coating which is white or matches the color of the light-generating sources. If a metal is used as the material, the diffusive properties may be achieved by roughening the reflective surface.

The flexible substrate may be coated, cast, deposited, or otherwise adhered to the conductive tracing or vice versa. In a preferred embodiment, the conductive tracings are directly adjacent to and in contact with the flexible substrate. Alternatively, one or more additional layers may be present between the conductive traces and flexible substrate, such as when adhesive are used. The conductive tracings may comprise a variety of materials, including rolled-annealed copper, electro-deposited copper, silver, nickel, gold, aluminum, iron, steel, solder, or any other metal or conductor. The conductive coating may be applied as, processed into, tracings using any means for application or removal, including chemical, mechanical, and optical means, as well as the use of lasers. In a preferred embodiment, a plurality of pairs of parallel conductive traces are etched into the rolled-annealed copper coating of a flexible substrate, for example, using conventional photo-etching techniques.

Polymer thick films including one or more finely divided conductive materials like silver, nickel, or carbon in a polymer binder like polyester, epoxy, acrylic, or vinyl also may be used. Polymer thick film printed wiring is less expensive than copper conductors since it is generally formed in a single step using screen printing, without traditional plating, etching, stripping, and cleaning. Examples of polymer thick films which offer an alternative to other types of circuitry are available from DuPont as the CB® series polymer thick film pastes.

If an adhesive is used to secure the conductive tracings or reflector to the substrate, consideration should be given to the thermal properties of the adhesive. Desirably, the adhesive is highly heat conductive to further facilitate conduction of the heat generated by the light-generating sources throughout the substrate and to adjacent heat sinks.

An insulating film or coating may be applied over the conductor surface to protect the circuitry from moisture, contamination, and conductor damage, and to reduce stress on the conductors during flexing. These protective coatings may be overlays comprising an insulating film coated with an adhesive, a coating comprising liquid polymers applied to the circuit, leaving the pad areas exposed, and solder masks comprising film laminates into which conductor access holes have been formed. Adhesive such as epoxies and polyimide resins may be used for overlays and laminations.

The light-generating source preferably is a light-emitting diode (LED) chip or die of the surface mount variety. Alternatively, other types of LEDs, lasers, and laser diodes also may be suitable. The light-generating sources may be multicolored LEDs, or a combination of multiple colored LEDs, a combination of different LEDs, or arrangement of the same type of LEDs, depending on the desired color, distribution or pattern.

For the treatment of neonatal hyperbilirubinemia, the preferred color of LEDs is blue, although green LEDs also may be effective. The treatment of other conditions may require different colored LEDs. For example, herpes may be most effectively treated by red LEDs, seasonal affective disorder may be treated by white or yellow LEDs, and psoriasis may be treated by ultraviolet LEDs.

The illuminator of the present invention may include any suitable interconnection technology to provide an electrical circuit among the LEDs, the substrate, the power supply, and any control device. In this regard, flexible or traditional wiring, solder attachment, conductive pieces, and/or pressure connectors may be used. A preferred embodiment utilizes surface mount technology to adhere the light-generating sources to the flexible substrate. Such manufacturing technologies may comprise surface mount-on-flex (SMT), chip-on-flex (COF), flip chip-on-flex (FCOF), micro-surface mount technology (micro SMT), micro-ball grid array (micro BGA), controlled collapsed chip connection (C4), or any known method of manufacture of assembly.

The illuminator may comprise a controller capable of making the light-generating sources separately addressable so that they may be selectively illuminated in a particular pattern to achieve a particular therapeutic result. In addition, the power level of one or all of the light-generating sources may be controlled to optimize the light intensity required, to mix colors where different LEDs are used, or to shut off light-generating sources in the case of overheating. In the latter instance, thermocouples may be provided in and around the light-generating sources, or on the contact surface, to monitor the temperature of the illuminator and provide feedback to the controller. Finally, the illuminator controller may contain a timer to assist in metering exposure of the patient according to doctor's instructions.

The interface of the illuminator preferably occupies the space between the substrate and the external contact surface. The interface may contain fins, vanes, ridges, grooves, tubes, holes, channels, or other features to absorb, transmit, or diffuse heat, to increase surface area for heat exchange, and/or to control or direct a flow of air, water or other fluids. Alternatively, the interface may be solid if heat is not a concern.

As will be apparent from the structural variations shown in the drawings and described below, the illuminator may include holes or spaces through the substrate, covering, or between the covering and substrate in locations which avoid interference with the conductive traces, light-generating sources, and cooling fluids. The illuminator may include a system of passive or active cooling. With active cooling, a cooling medium is propelled through internal channels using a blower or pump. The cooling medium in this regard may be in liquid or gaseous form, with air being preferred to avoid increasing the weight of the illumination in use. Another less-expensive variant is passive cooling wherein air or other cooling medium is provided in the internal spaces defined by the interface.

The interface preferably diffuses the light generated by each discrete light-generating source so as to provide a less focused emittance. In addition, where a plurality of discrete and spaced apart light-generating sources are provided, the interface preferably diffuses the individual points of light to provide a more uniform emittance.

More broadly, at least a portion of the interface preferably causes the light emitted by the plurality of light-generating sources to be diffused or directed as desired. Such diffusion or direction is effective to provide a more uniform, constant and intense light pattern on the contact surface relative to a similar apparatus including a plurality of discrete light emitting sources without light diffusion. Therefore, the interface may be made of a single material or blend of materials having different refractive indices, such as silicone and glass bubbles or silicone and titania, or may include other materials, such as metals, to reflect or block light.

Alternatively, or in addition, an outer covering or an internal layer may be provided with deformities or markings formed by mechanical, chemical, or other means to cause light emitted by the light-generating sources to diffuse. Such deformities or markings can be formed by molding, cutting, hot stamping, etching, painting, machining, coating, forming, milling, or printing. The deformities may vary in density, opacity, shape, color, index or refraction, size, depth and shade so as to produce a desired diffusion or light distribution. In one embodiment, such surface deformities are created by roughening the surface of the cover mold with glass beads or sand so as to give the surface an uneven or matte finish. The interface, such as the covering, may vary in color, index or refraction, or shape along the length of the illuminator.

A reflector of reflectors may be used to diffuse light. Lambertian reflectors are often preferred. Prismatic films and diffusers, lenticular lenses, coatings, and other systems or materials may be used to cause light to be diffused as desired. Reflective paints or coatings, such as coatings of titania, magnesium oxide, aluminum oxide, other white powders and the like and mixtures thereof, are useful for diffusion. Reflective or refractive elements may be provided on or in the substrate, the interface, the covering, or combinations thereof. Reflective or refractive elements on or in the covering are often useful to redirect a portion of the light emitted by a light source away from the patient and towards the interface or substrate so that it may ultimately be redirected towards a more desirable location on the patient. Reflecting or refracting means on or in the covering, the interface, and/or the substrate, may be conveniently adapted to work in combination with each other to diffuse, block, and/or distribute light as desired.

The interface may be made of silicone, urethane, polyurethane, or any flexible plastic or other translucent or transparent material, or colored material, on combinations thereof. As mentioned above, silicone with at least a portion having glass bubbles and/or titania impregnated therein is often preferred.

Having described the invention in some detail, the following is a presentations of more specific embodiment of the invention illustrated in FIGS. 2–18D.

Figure 2:
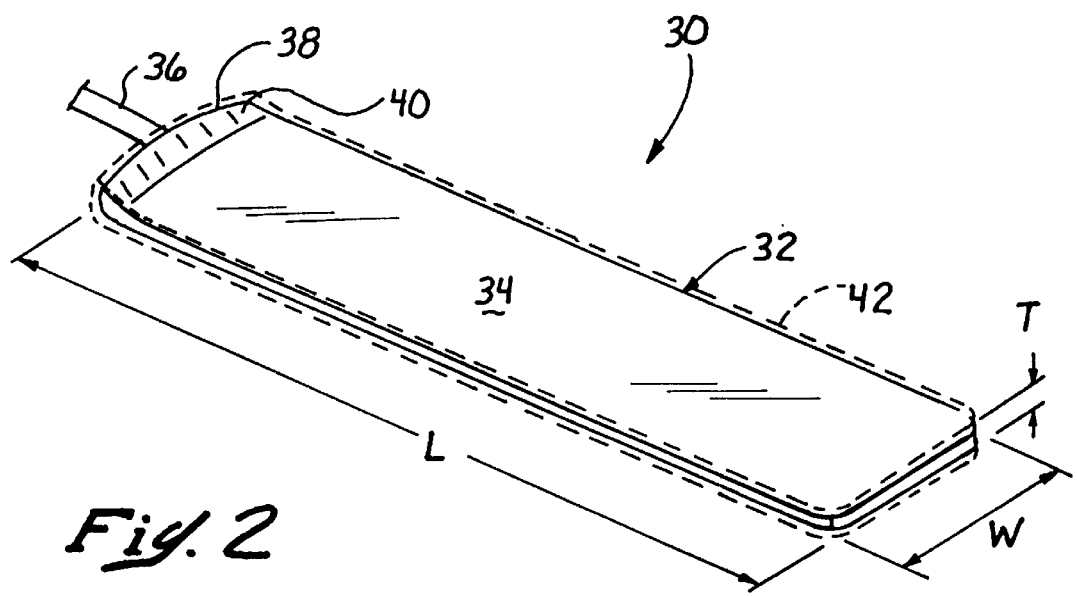
FIG. 2 is a perspective view of a flexible mat-type illuminator of the present invention.
Figure 3:
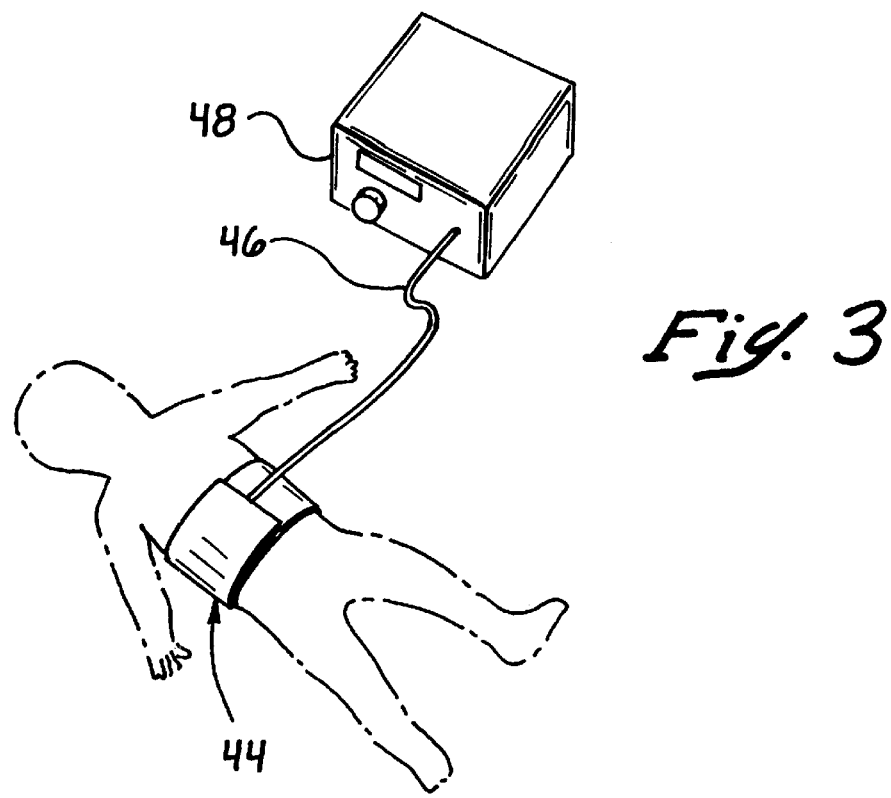
FIG. 3 is a schematic view of a phototherapy system utilizing a flexible mat-type illuminator of the present invention.
Figure 3A:
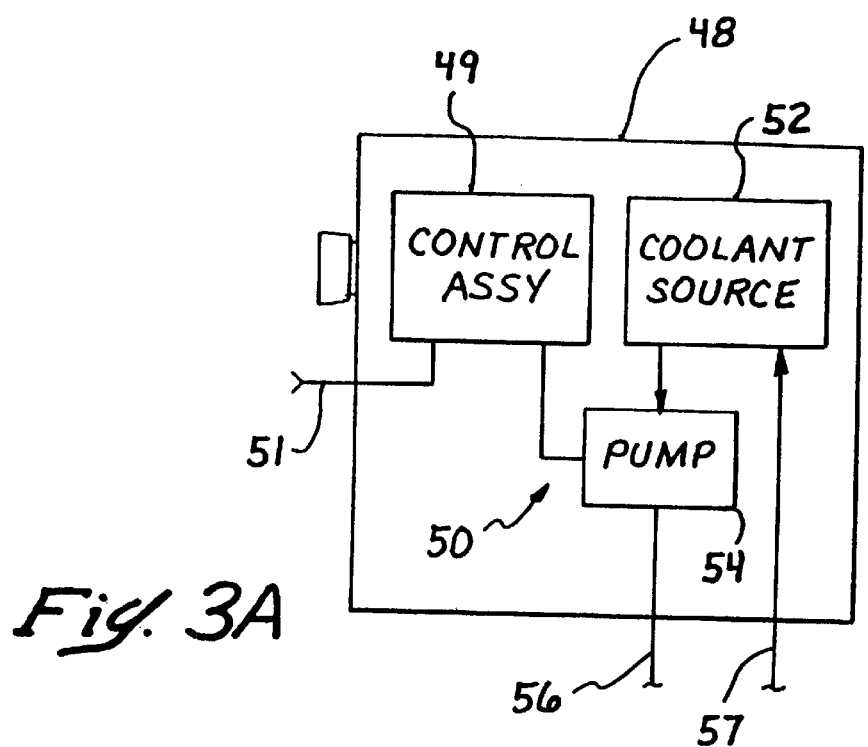
FIG. 3A is a schematic illustration of the control housing of the phototherapy system shown in FIG. 3.
Figure 5:
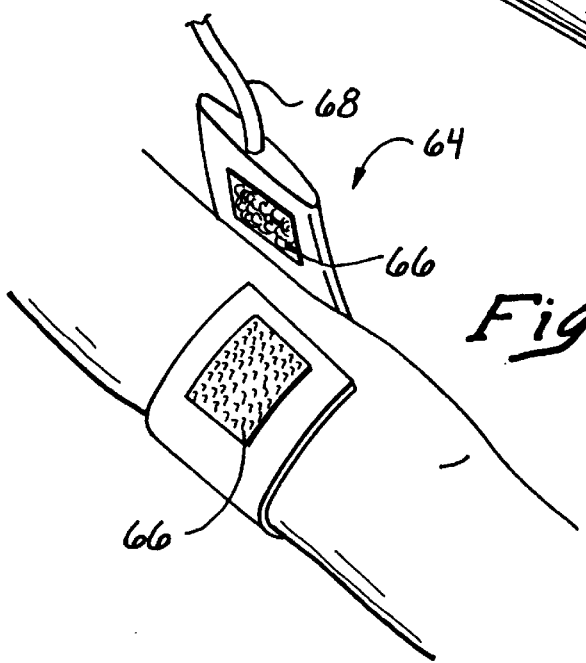
FIG. 5 is a perspective view of a flexible mat-type illuminator of the present invention wrapped around an adult limb.

FIG. 2 illustrates an illuminator 30 of the present invention comprising an elongate, planar, flexible body 32 having a front or contact surface 34 and a back surface facing the opposite direction and not seen in FIG. 2. In the embodiment illustrated, the illuminator 30 has a rounded rectangular configuration with a length L, a width W, and a thickness T, with the length L being substantially greater than the width W, both of which are substantially greater than the thickness T. The proportion of these dimensions is preferred to enable the illuminator 30 to be wrapped around a small infant, or around the limb of an adult, and cover substantial surface area, as seen in FIGS. 3 and 5. Of course, those of skill in the art will understand that other configurations are possible.

As will be describe in more detail below, the illuminator 30 contains a plurality of electric light-generating sources, and thus a power cable 36 attaches to a first narrow end 38 of the body 32. The body 32 is thicker in a region 40 adjacent to the first end 38 to provide strain relief at the interface between the body and cable 36. In one particular preferred embodiment, the body 32 is molded around the light-generating sources and power cable 36, with the thickened region 40 being formed accordingly. Alternatively, a higher durometer or stiffer material may be used on the end of the illuminator and/or near the end of the cable to provide the strain relief. As will also be described below, the illuminator 30 may include means for transferring heat away from the front surface 34, which may involve flow of a cooling medium to interior channels formed in the body 32. In that case, the jacket around the power cable 36 may also provide a conduit for delivery of the cooling medium to and from the illuminator 30.

As seen in phantom in FIG. 2, the illuminator 30 is desirably at least partly surrounded with a disposable overwrap 42 as a contamination barrier between the illuminator and the skin of the patient. Such an overwrap 42 may be thin biocompatible polymer, such as polyethylene, polyurethane or cellophane, and is preferably transparent (or at least translucent) so as not to substantially reduce the intensity of light transmitted to the patient. Additionally, the overwrap 42 may have heat insulating and/or light diffusing properties. The overwrap 42 is preferably loosely fitted over the illuminator in any form, and can be easily secured by tape, elastic or other means, and thus easily removed and disposed of for sanitary purposes. The illuminator can then be immediately re-used with a second overwrap 42.

FIGS. 3, 3A, 4, 5 and 5A illustrate several potential configurations of the illuminator of the present invention. In FIG. 3, an illuminator 44 similar to that shown in FIG. 2 is wrapped completely around the abdomen of an infant patient. The illuminator 44 may be secured in this position using straps, Velcro, adhesive tape adhered to a disposable cover, or other such attachment means. A cable 46 supplies electricity and cooling medium from a control housing 48 to illuminator 44, as mentioned above. FIG. 3 schematically illustrates a control assembly 49 (of conventional design) providing electricity to illuminator 44 through power conduit 51. Control assembly 49 also controls the operation of an active cooling system 50 including a source of cooling medium 52 and a pump 54. Source 52 may include cooling coils or other suitable assembly for maintaining the temperature of the cooling medium or coolant at a desired level. A pair of conduits 56 and 57 deliver the cooling medium to the illuminator 44 and return medium to be cooled to the system 50.

Figure 4:
FIG. 4 is a perspective view of alternative mat-type illuminator of the present invention.

FIG. 4 illustrates a larger, mat-type illuminator 60 upon which an infant may be placed. A single cable 62 supplies power (and possibly cooling medium) to the illuminator 60.

FIG. 5 illustrates a mat-type illuminator 64, much like the illuminator 30 illustrated in FIG. 2, that is wrapped around the patient's limb and fastened with Velcro hook/loop fastener patches 66. Again, a single conduit 68 delivers power and potentially cooling medium to the illuminator 64.

Figure 5A:
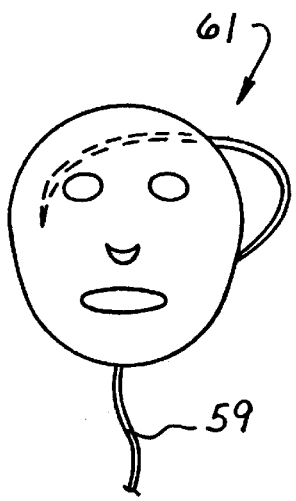
FIG. 5A is an illustration of an illuminator of the present invention in the form of a mask to be worn on the face of an adult or adolescent human.

FIG. 5A illustrates a further specialized form of an illuminator in accordance with the present invention. This illuminator 61 is in the form of a mask to be placed on the face of an adult or adolescent human. An elastic band 63 is attached to mask 61 and is used to secure the mask in a desired portion on the face. Eye holes 65, nose hole 67 and mouth hole 69 are optionally provided so that the eyes can be protected from the light and normal breathing/talking can occur while the patient is being treated, for example, for acne. A single conduit 59 delivers electrical power and possibly cooling medium to the mask 61.

The illuminator may be formed into a variety shapes, such as a pad or mat shown, and may be formed into any suitable configuration to treat various medical conditions, as described herein, while also protecting the patient from unwanted, and possibly harmful exposure to light and/or heat. For example, the present illuminators can be configured to be placed on the face, like a wash cloth, for the treatment of seasonal affective disorder, as well as acne and other skin conditions; or can be configured similarly to a sanitary napkin, tampon or condom for the treatment of herpes. Alternatively, the illuminator can be formed into a belt, a wrap, a cushion or pillow, a collar, a blanket, a strap, a vest, or any other desired shape. Advantageously, the particular shape and ultimate configuration on the patient does not affected the quality and intensity of the light delivered, as with prior fiber optic devices. In short, the forms of the present illuminators illustrated are not intended, and should not be taken, to be limiting.

Figure 6:
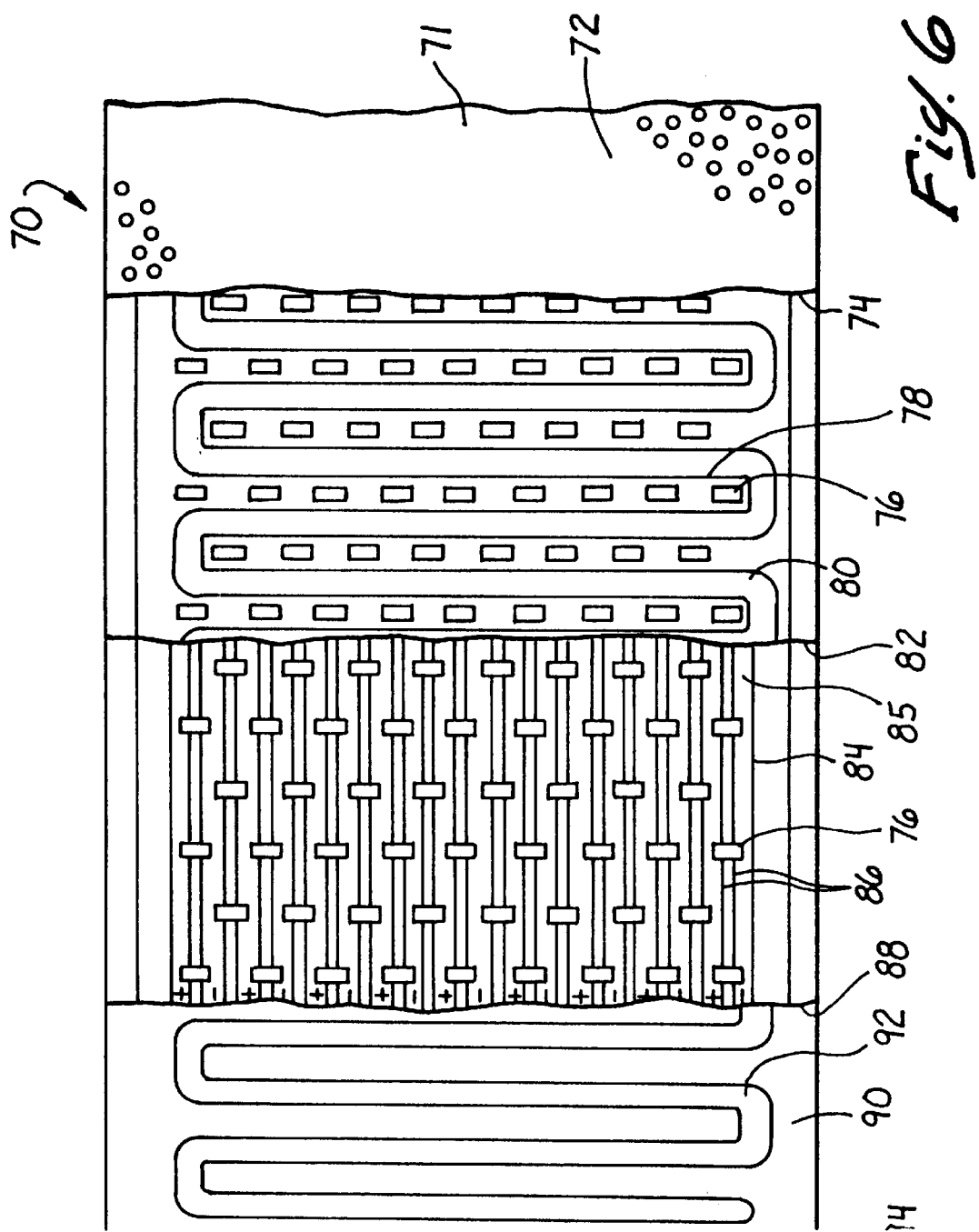
FIG. 6 is a plan view of a mat-type illuminator of the present invention showing sequential layers cutaway.

FIGS. 6–7 illustrate the internal construction of an exemplary illuminator similar to that shown in FIG. 2. The plan view of FIG. 6 shows one end of the body 70 of the illuminator with sequential layers stripped away from right to left. These layers can be seen in cross-section in FIG. 7. The front or contact surface 71 of the body 70 faces out of the page in FIG. 6. Therefore, a front covering 72 is seen on the right side of FIG. 6, and is cut away at line 74 to reveal an array of light-generating sources 76. A plurality of glass bubbles 73 (right side of FIG. 7) are randomly located in front covering 72 to scatter or diffuse light, as discussed herein.

In this embodiment, a plurality of transversely extending spaces 78 surround the sides of each of the light-generating sources 76, and are spaced from one another to provide cooling channels 80 therebetween. The spacers 78 may or may not at least partially encapsulate the sources 76. Encapsulation is often preferred to enhance dissipation of heat and light diffusion, and to protect the light-generating sources from physical damage and/or detachment. As is apparent from FIG. 6, the cooling channels 80 extend in a serpentine fashion along the length of the body 70.

The layer of spacers 78 is cut away at line 82 in FIG. 6 to reveal a substrate 84 on which the light-generating sources 76 are mounted. In addition, an array of conductive traces 86 is provided on the substrate 84 to power the light-generating sources 76. A reflector 85, also seen in FIG. 7, may be provided on the substrate 84 and around the light-generating sources 76. The reflector 85 is desirably a thin layer of material adhered to the substrate 84 and having perforations at the locations of the light-generating sources 76. Alternatively, the substrate material itself may be reflective, or the reflector may be coated on the substrate.

Continuing to the left in FIG. 6, the substrate layer is cut away at line 88 to reveal a layer of secondary spacer material 90 within which is formed a secondary cooling channel 92. Again, the cooling channel 92 extends in a serpentine fashion along the length of the body 70 and adjacent to the substrate. Finally, the secondary spacer material 90 is cut away at line 94 to reveal a back cover 96.

Now with reference more particularly to the cross-section of FIG. 7, the illuminator can be viewed more generally as including the light-generating sources 76 mounted on the substrate 84, and an interface provided between the substrate 84 and a front or contact surface 98. In the illustrated embodiment, contact surface 98 comprises the outer surface of the covering 72, while the interface comprises a combination of the covering, the spacers 78, and the cooling channels 80. In addition, the illuminator preferably includes a backing, which in this embodiment comprises the secondary spacers 90, secondary cooling channels 92, and back cover 96. The invention may be best described in terms of the preferred functional characteristic of the interface and the backing, as follows.

As mentioned above, the interface preferably performs two main functions: heat insulation and light diffusion. That is, the separate light-generating sources 76 generate some heat in operation which must be intercepted and carried away or attenuated before it reaches the contact surface 98. Therefore, the interface preferably provides a thermal barrier to heat conduction, and may also include a system of passive or active cooling, facilitated by the cooling channels 80. In addition, the light-generating sources 76, being discrete and spaced apart, create a plurality of points of intense light, rather than an even distribution. Therefore, the interface preferably diffuses the discrete points of light to provide a more uniform emittance. In addition, the interface performs other functions. For example, the interface protects the light-generating sources and circuitry from damage and/or detachment, reduces or even eliminates the risk of exposing the patient to electrical current, and provides additional padding to enhance the comfort of the patient.

The backing preferably performs two main functions as well: heat conduction and light reflection. That is, the backing preferably provides an effective heat sink for the heat generated by the light-generating sources 76, which works in conjunction with the heat barrier provided by the interface to cause heat to travel away from the contact surface 98. In this manner, the secondary spacer 90 is preferably made out of a highly conductive material that is in intimate contact with the backside of the substrate 84. The backing also protects the circuitry and light-generating sources, protects the patient from electrical current and provides added padding to enhance patient comfort.

As will be apparent from the variations in construction that follow, numerous combinations of the interface and backing are possible. Because of the numerous configurations that the illuminator can take, as seen for example in FIGS. 3–5, there is no single optimum construction, but rather the functional characteristics described above are desirably provided in the most cost-effective manner for the particular application. Thus, for example, if the illuminator is to be used as a mat, as seen in FIG. 4, additional padding between the substrate 84 and light-generating sources 76 may be required, which will increase the thickness of the interface and/or backing. Similarly, for an elongated mat-type illuminator, as seen in FIGS. 2–3 and 5, padding is not as important as the illuminator being flexible and lightweight. Additionally, the contact surface of the illuminator preferably is soft and hypoallergenic, especially if it is to be used for treatment of hyperbilirubinemia in neonates.

FIG. 8 illustrates, in cross-section, an illuminator 100 having a substrate 102 with a plurality of light-generating sources 104 mounted thereon. The illuminator 100 is very similar to that shown in FIG. 7, but has a different covering configuration. An array of spacers 106 between cooling channels 108, as in FIG. 7, is provided. In addition, a thermal insulating layer 110 and outer covering 112 are included in the combination of components making up the interface. Also included are a plurality of glass bubbles 111 located in a relatively well defined layer in outer covering 112 to scatter or diffuse light, as discussed hereinafter. As with FIG. 7, the backing comprises the secondary spacer 114 and secondary cooling channels 116 encompassed by the back cover 118. The insulating layer may comprise air, a thermally insulating, light transmitting polymer, or a vacuum. The insulating layer 110 may comprise a substantially transparent multilayer thin film of dielectric materials having indices of refraction different from each other(e.g., titania and silica), a layer of which is approximately the thickness of a quarter wavelength of infrared radiation emitted by the light source. Alternatively, or in addition, the insulating layer 110 may comprise a substantially transparent thin film of metals(e.g., silver, chromium, nickel, tantalum, or titanium, or alloys thereof), or a combination of metals and dielectric materials, configured to reflect such heat. The addition of an insulating layer 110 further helps to prevent heat transfer from the light generating sources 104 to the contact surface of the illuminator. In this regard, the glass bubbles 73 randomly located in front covering 72, as seen in FIG. 7, act as a light diffuser and also as an insulator.

As mentioned above, at least a portion of the interface as seen in FIGS. 7 and 8 preferably causes the light emitted by the plurality of light-generating sources to be diffused. Thus, as seen in FIG. 7, the front cover 72 comprises a matrix of silicone within which a plurality of glass bubbles or titania is randomly impregnated. Alternatively, scattering elements may be impregnated in greater quantities above the light-generating sources than between them so as to scatter more light where its intensity is greater. FIG. 8 illustrates a cover 112 which comprises a matrix of silicone having a plurality of more evenly distributed glass bubbles or titania 111. It should be noted that the size of the glass bubbles in the figures is exaggerated for illustration purposes. Alternatively, or in addition, the covering 72 or 112, or the insulating layer 110, may be provided with deformities or markings formed by mechanical, chemical, or other means to cause light emitted by the light-generating sources to diffuse.

The interface may also comprise filters to reflect or absorb certain wavelengths of light. In order to control the exposure of the patient to ultraviolet radiation, or to minimize the deteriorative effect of such radiation on the illuminator, a layer or coating of or containing an ultraviolet absorber may be used. For example, the insulating layer 110 shown in FIG. 8 may instead represent an ultraviolet filter. Examples of ultraviolet absorbers include benzophrenones, benzotriazoles and salicylates. In addition, the illuminator made further comprise additives, including infrared absorbers (e.g., metals), antioxdants, coloring agents, plasticisizers, stabilizers, and antistatic agents.

Figure 9:
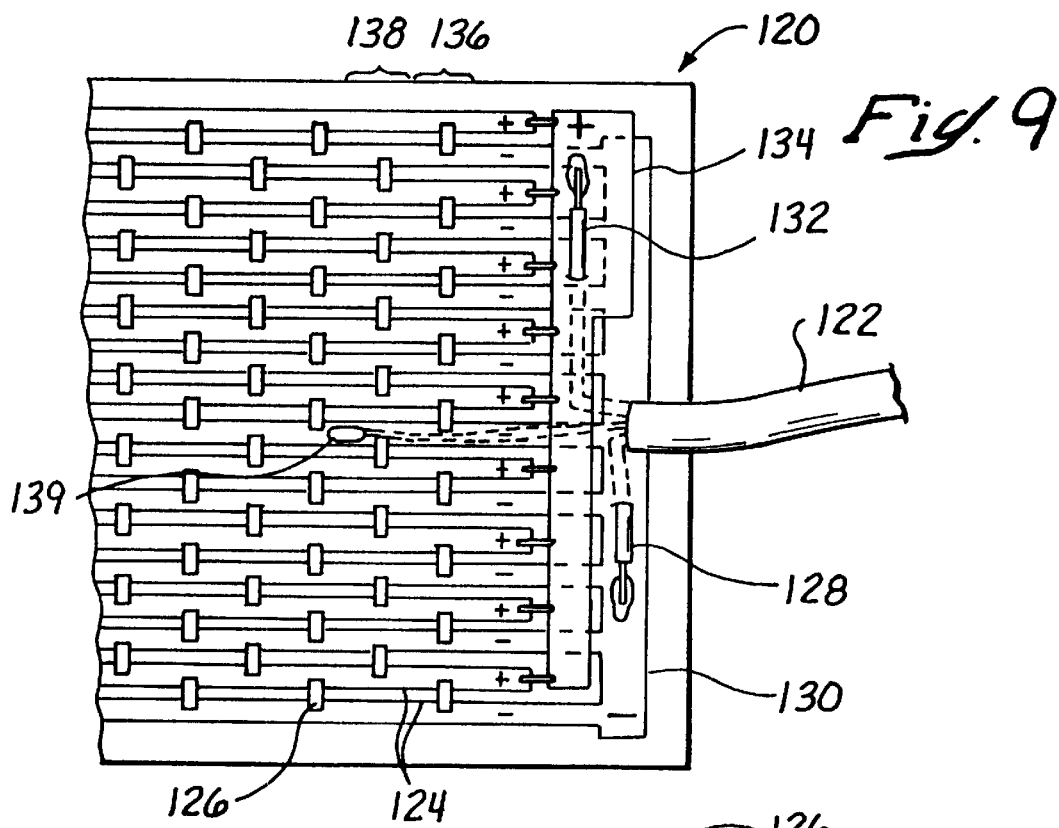
FIG. 9 is a plan view of a substrate and electronic connections for a plurality of light-generating sources used in an exemplary illuminator of the present invention.

FIG. 9 is a cutaway view of one end of a illuminator 120 of the present invention showing the interface between a power cable 122 and an array of conductive tracings 124 providing a conductive path to a plurality of light-generating sources 126. A wire 128 electrically connects to a pole 130 that is in electrical communication with the negative terminal of each of the light-generating sources 126. Likewise, a wire 132 electrically connects to a pole 134 that is in electrical communication with the positive terminal of each of the light-generating sources 126. The wires may be electrically connected to the tracings by lap soldering to the pole or bus bar or through use of DIMM or MOLEX-type multiconductor connectors. In this embodiment, the light-generating sources are provided in seventeen rows across the width of the illuminator 120, and are staggered from column to column. That is, a first column 136 of nine light-generating sources is followed by a second column 138 of eight light-generating sources in different rows of conductive tracings 124. This pattern repeats itself along the length of the illuminator 120.

FIG. 9 also shows a pair of conductive wires passing through the power cable 122 and connecting to a temperature sensor 139. The temperature sensor 139 may be a thermocouple, and is desirably mounted in the illuminating field of light-generating sources. In addition, although not shown, the temperature sensor 139 is preferably mounted in the covering proximate to a skin contact surface of the illuminator so as to monitor the temperature of the illuminator at that location. This positioning provides feedback to a control system, such as the control assembly 49 seen in FIG. 3A, regarding the skin contact surface temperature of the illuminator. If the skin contact surface temperature exceeds a predetermined value, such as for example about 110° F., the control system can either shut off power to the light-generating sources and/or increase the cooling flow if an active cooling system is used. In an exemplary embodiment, the illumination has a maximum skin contact surface temperature of about 115° F., preferably below 110° F., more preferably below 105° F., and most preferably below 110° F.

Figure 10:
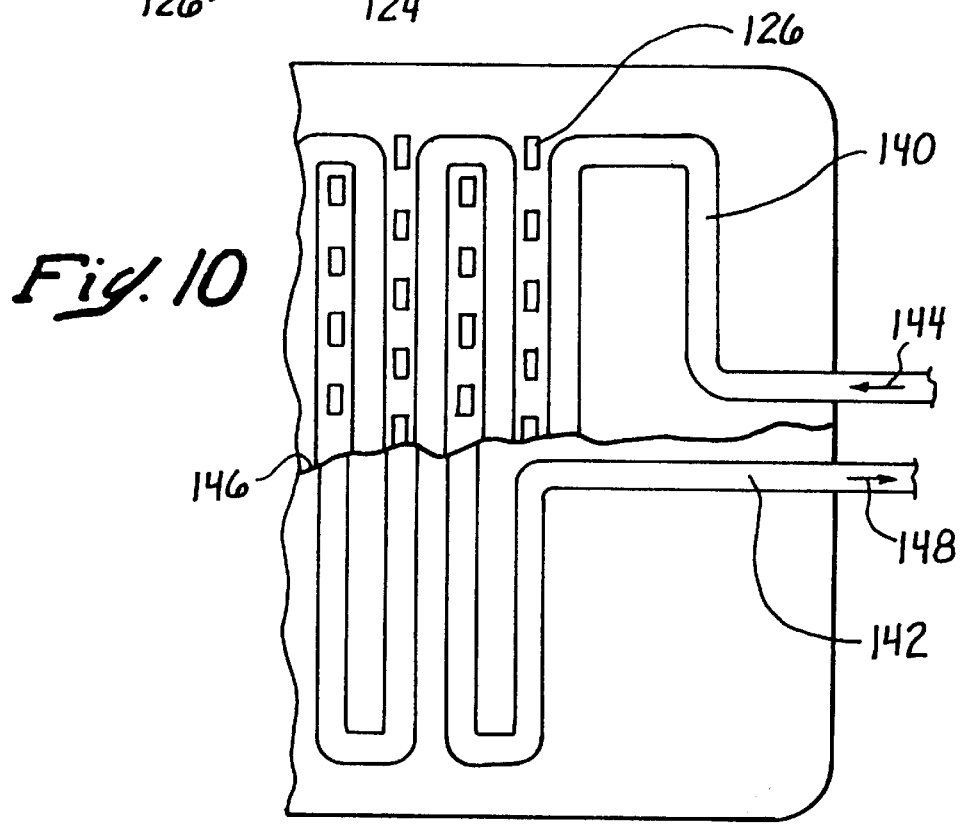
FIG. 10 is a partial cutaway view of internal cooling channels formed in an exemplary illuminator of the present invention.

FIG. 10 illustrates the relative positions of the light-generating sources 126, a first cooling channel 140, and secondary cooling channel 142 provided below the substrate. Arrow 144 indicates an inflow of cooling medium to the first cooling channel 140, which medium flows between columns of light-generating sources 126. The horizontal cutaway line 146 reveals the secondary cooling channel 142 below the substrate. Although not shown, the first cooling channel 140 is in fluid communication with the secondary cooling channel 142 at the opposite end of the illuminator. That is, the cooling medium flows along the length of the illuminator 120 (from right to left), and then passes across the plane of the substrate (i.e., into the page) through an opening into the secondary cooling channel 142. The cooling medium then flows (from left to right) along the length of the secondary cooling channel 142 until it exits the illuminator, as indicated by arrow 148.

FIG. 10 thus illustrates active cooling of the illuminator 120, wherein cooling medium is propelled through internal channels. The cooling medium in this regard may be in liquid or gaseous form, with air being preferred to avoid increasing the weight of the illuminator 120 in use. Of course, other arrangements of cooling means are possible, as will be described in more detail below.

FIGS. 11–13 illustrate various cross-sections of illuminators in accordance with present invention showing the basic elements of a substrate, a light-generating source (in this case an LED), an interface between the substrate and a contact surface, and a backing. Consistent with the discussions above, these variations are helpful in illustrating the multiple permutations of materials and configurations that are possible in constructing an illuminator of the present invention.

FIGS. 11A–11D illustrates four cross-sections that all have a substrate 160, an LED 162, and an interface comprising a solid layer 164 of light-diffusing and heat-insulating material. The layer 164 has an exterior skin contact surface 166. One example of material for the layer 164 is silicone having glass bubbles distributed randomly throughout. Another example of material for the layer 164 is silicone having titania distributed throughout. Alternatively, or in addition, the layer 164 may be silicone having a matte finish on the skin contact surface 166. The skin contact surface may have a pattern, for example, a printed pattern, effective to scatter and diffuse light.

Figure 11A:
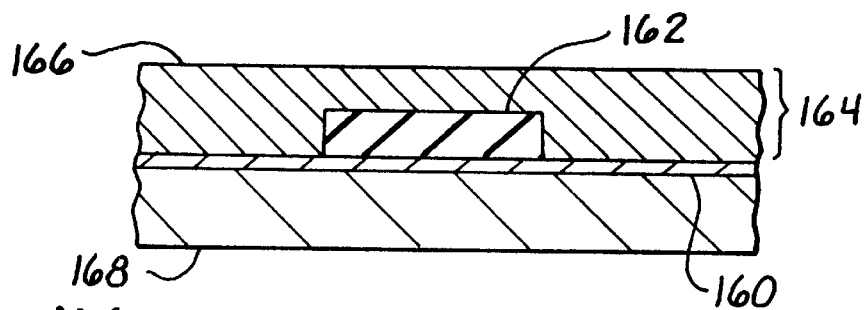
FIGS. 11A–11D are cross-sectional views showing various constructions of the illuminator of the present invention.
Figure 11B:
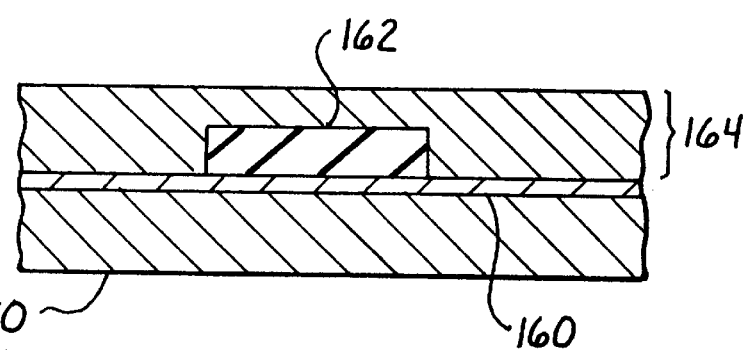
Figure 11C:
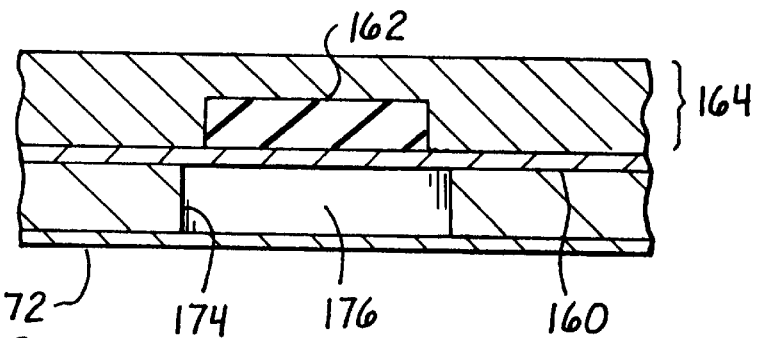
Figure 11D:
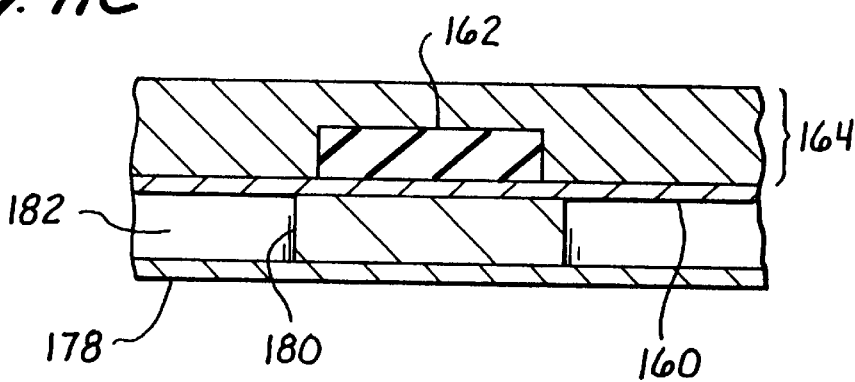

In FIG. 11A, the backing comprises a solid layer 168 of light-reflective, heat-conductive material. FIG. 11B includes a backing comprising a solid layer 170 of light-diffusive, heat-conductive material. In FIG. 11C, the backing comprises a back cover 172 spaced from a substrate 160 with a secondary spacer 174. The secondary spacer 174 includes a gaps or channels 176 therein directly across the substrate 160 from each of the LEDs 162. In FIG. 11D, the backing comprises a back cover 178 spaced from the substrate 160 with a secondary spacer 180. In this case, the secondary spacer 180 is provided directly underneath each of the LEDs 162, and preferably is made of a highly heat conductive material. Heat thus flows from the LED 162 through the substrate to the secondary spacer 180, which is cooled on either side by the gaps 182.

FIGS. 12A–12F all include the substrate 160, LED 162, and a front cover 190 whose exterior surface is intended to contact the skin of patient. In addition, each of the cross-sections in FIGS. 12A–12F include one or more gaps or channels for cooling.

Figure 12A:
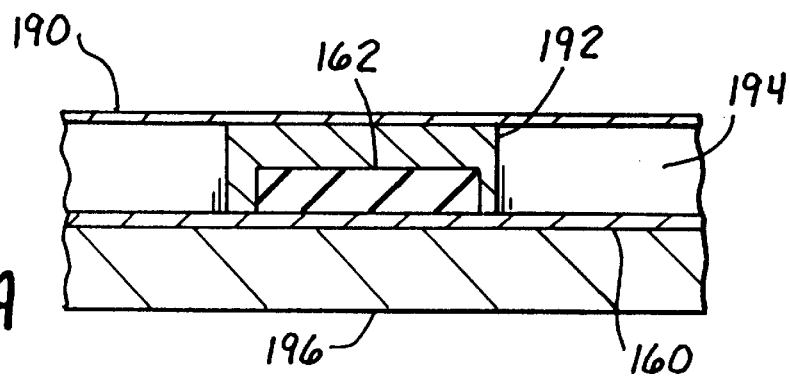
FIGS. 12A–12F are cross-sectional views showing further constructions of the illuminator of the present invention.
Figure 12B:
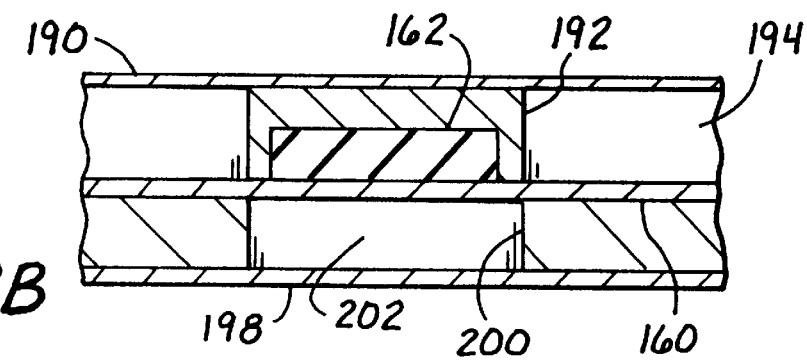

In FIG. 12A, the cover 190 is spaced from the substrate 160 with a spacer 192. The spacer 192 is formed directly over the LEDs 162 and defines gaps or channels 194. The backing desirably comprises a solid layer 196 of material. In FIG. 12B, the interface includes the aforementioned spacer 192 and channels 194, as in FIG. 12A, but the backing comprises a back cover 198 spaced from the substrate 160 with a secondary spacer 200. In this embodiment, the secondary spacer 200 provides gaps or channels 202 directly underneath each of the LEDs 162.

Figure 12C:
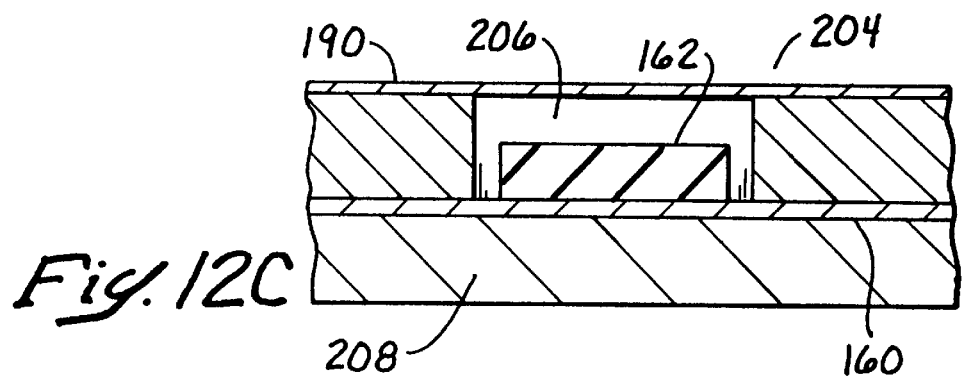
Figure 12D:
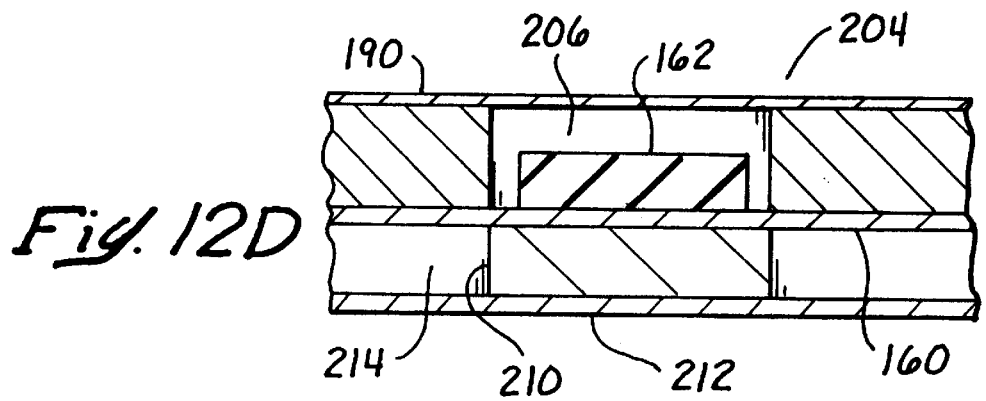

FIG. 12C shows a spacer 204 separating the cover 190 from the substrate 160, the spacer 204 providing gaps or channels 206 directly surrounding each of the LEDs 162. In this embodiment, the interface is formed by the cover 190, spacer 204, and channels 206, and the cooling medium can flow directly over each of the LEDs 162. Again, the backing is provided by a solid layer 208. FIG. 12D also illustrate the spacer 204 and channel 206, which together with the cover 190 comprise the interface, but the backing is provided by a spacer 210 and a back cover 212. The spacer 210 is directly underneath each of the LEDs 162 and forms gaps or channels 214 therearound.

Figure 12E:
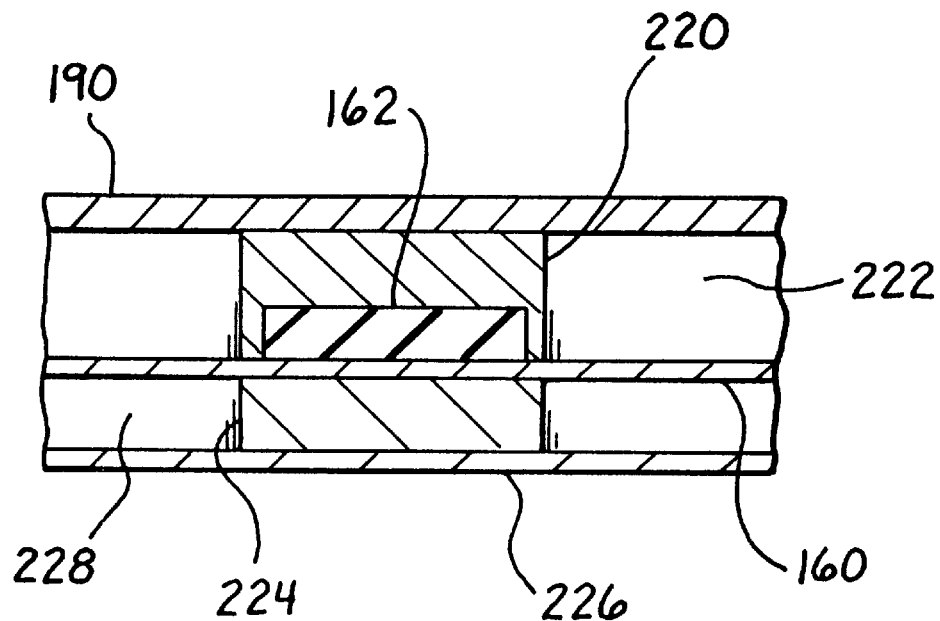
Figure 12F:
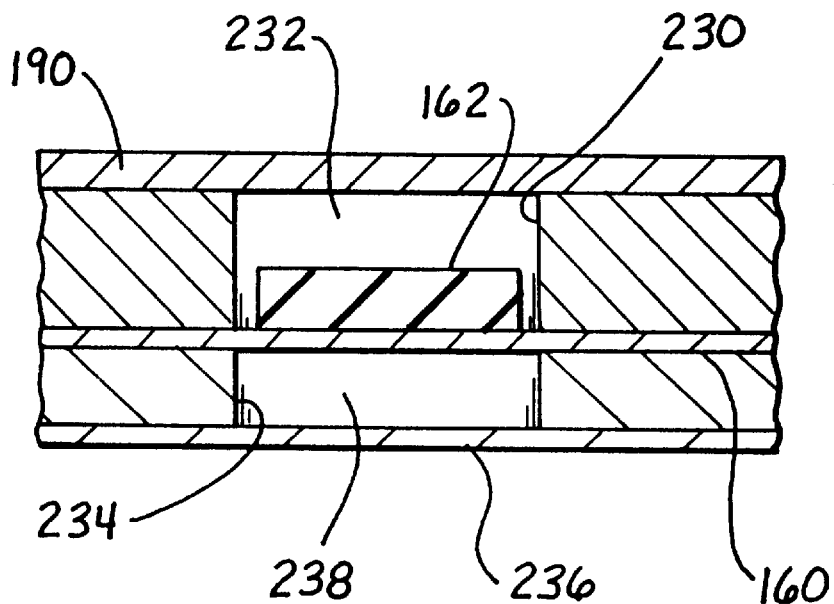

FIGS. 12E and 12F are substantial mirror images of one another, each of which having cooling channels above and below the substrate 160. In FIG. 12E, the interface comprises the cover 190, the spacer 220 directly surrounding each of the LEDs, and gaps or channels 222 defined by the spacer. The backing comprises a secondary spacer 224 directly underneath each of the LEDs 162, a back cover 226, and a plurality of gaps or channels 228 adjacent to the secondary spacer. In FIG. 12F, a spacer 230 separates the cover 190 from the substrate 160 and defines cooling gaps or channels 232 directly over each of the LEDs 162. The backing comprises a secondary spacer 234 separating a back cover 236 from substrate 160 and defining a plurality of cooling gaps or channels 238 directly underneath each of the LEDs 162.

FIGS. 13A–13D illustrates several illuminator cross section with maximum spaces defined by vanes or walls between two covers. More specifically, each of the cross-sections in FIGS. 13A–13D includes the substrate 160, LED 162, a front cover 250, and a back cover 252.

Figure 13A:
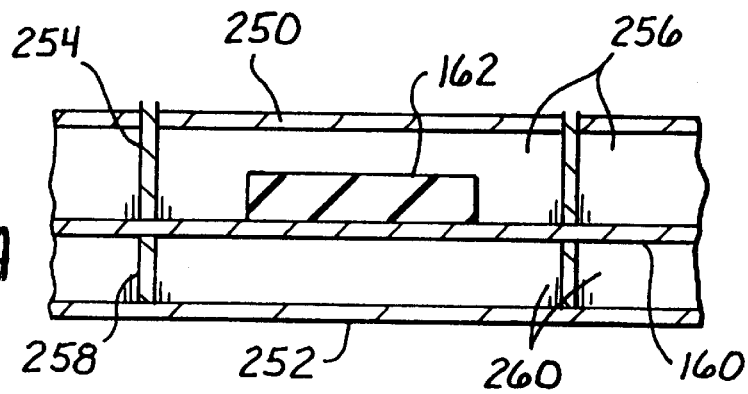
FIGS. 13A–13D are cross-sectional views showing still further constructions of the illuminator of the present invention.

FIG. 13A includes a plurality of vanes or walls 254 spacing the front cover 250 from the substrate 160. Cooling gaps or channels 256 are defined by the walls 254 surrounding each of the LEDs 162. The backing comprises the back cover 252 spaced from the substrate 160 by secondary walls 258. Again, and gaps or channels 260 are provided below the substrate for cooling purposes.

Figure 13B:
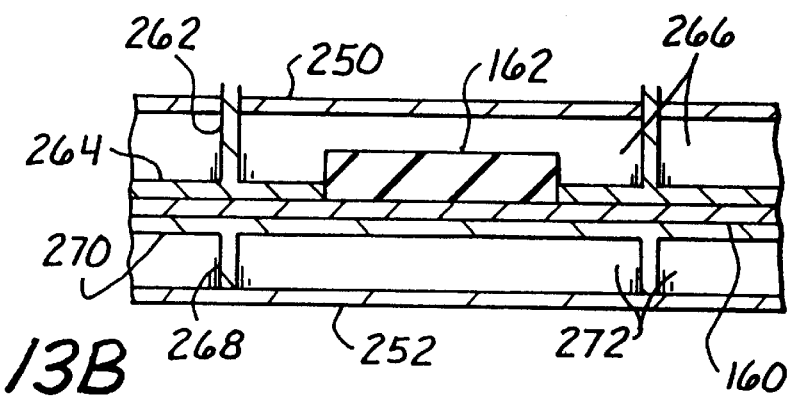

In the embodiment of FIG. 13B, walls 262 extend between the front cover 250 and a coating layer 264 provided on top of the substrate 160. The cooling layer extends into contact with each of the LEDs 162. As in FIG. 13A, the walls 262 defined gaps or channels 266 surrounding each of the LEDs 162. The backing comprises secondary walls 268 extending between the back cover 252 and a coating 270, and gaps 272 provided directly underneath each of the LEDs 162.

Figure 13C:
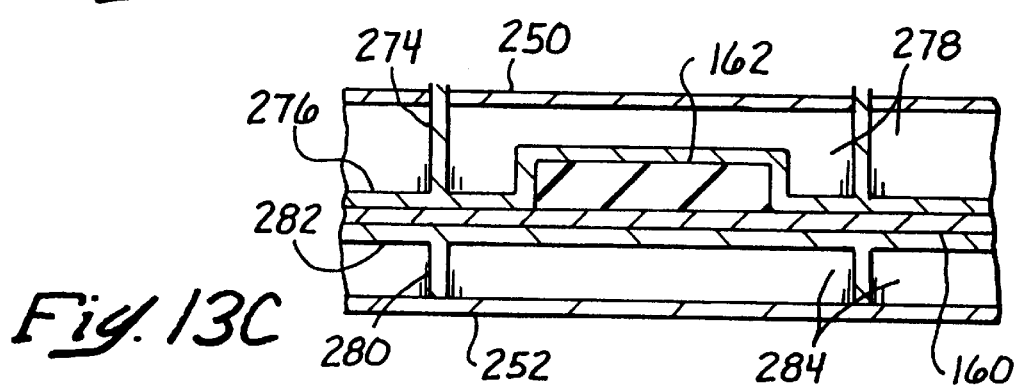

FIG. 13C is similar to that shown in FIG. 13B and includes walls 274 extending between the front cover 250 and a layer 276 formed on the substrate 160. In this case, the layer 276 completely covers each of the LEDs 162. Cooling gaps or channels 278 are formed over each of the LEDs, and the covering protects each of the LEDs from the corrosive effect of a fluid cooling medium. Also, as in FIG. 13B, the backing comprises secondary walls 280 spacing the back cover 252 from a layer 282 formed on the backside of the substrate 160. Again, cooling gaps 284 are provided below each of the LEDs.

Figure 13D:
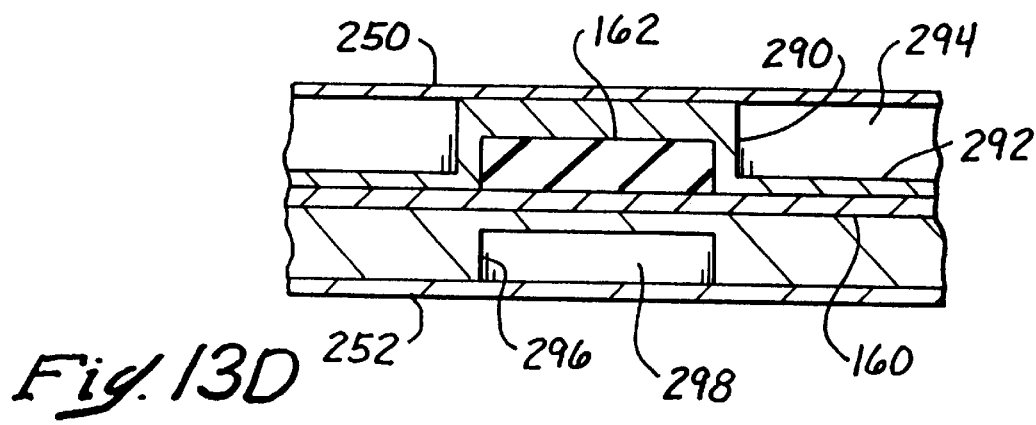

Finally, FIG. 13D includes a spacer 290 extending between the substrate 160 and a front cover 250. The spacer 290 covers the substrate 160, as at 292, but provides gaps or channels 294 for cooling. The backing comprises a secondary spacer 296 extending between the substrate 160 and the back cover 252, the spacer being generally solid but defining gaps or channels 298 directly below each of the LEDs 162.

Figure 14A:
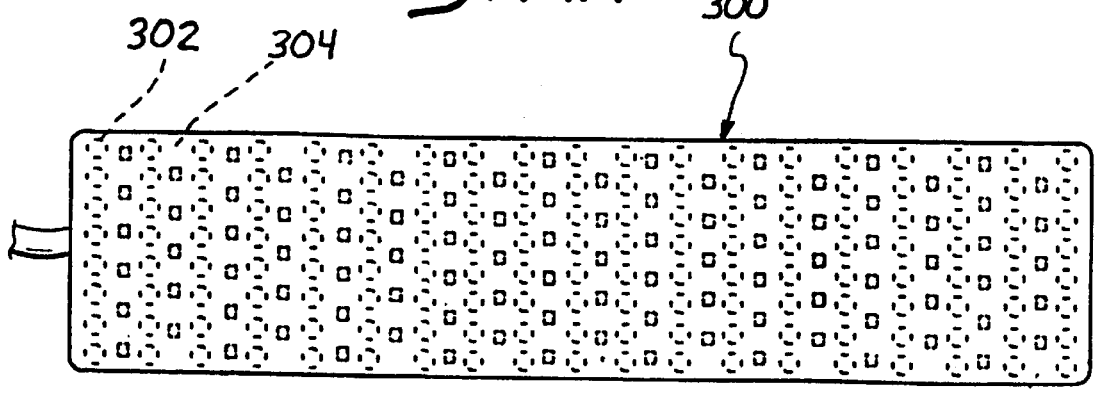
FIGS. 14A–14C are plan views of illuminators of the present invention having passive cooling channels therein.
Figure 14B:
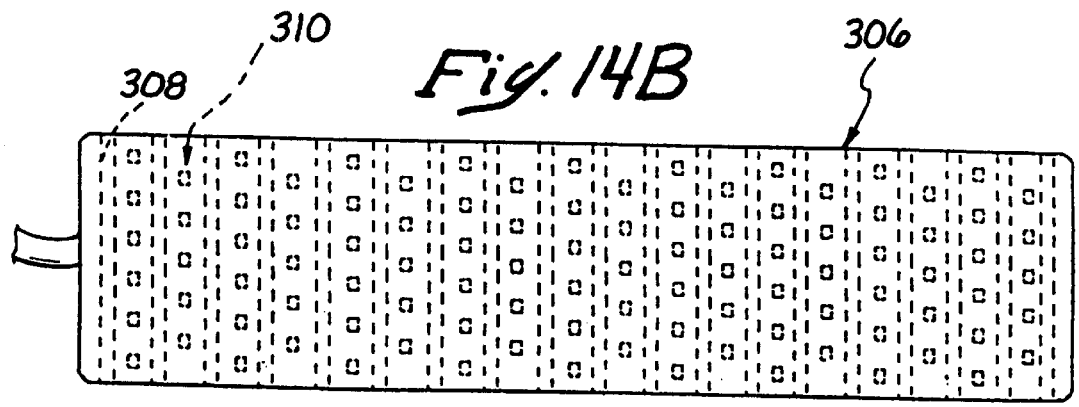
Figure 14C:
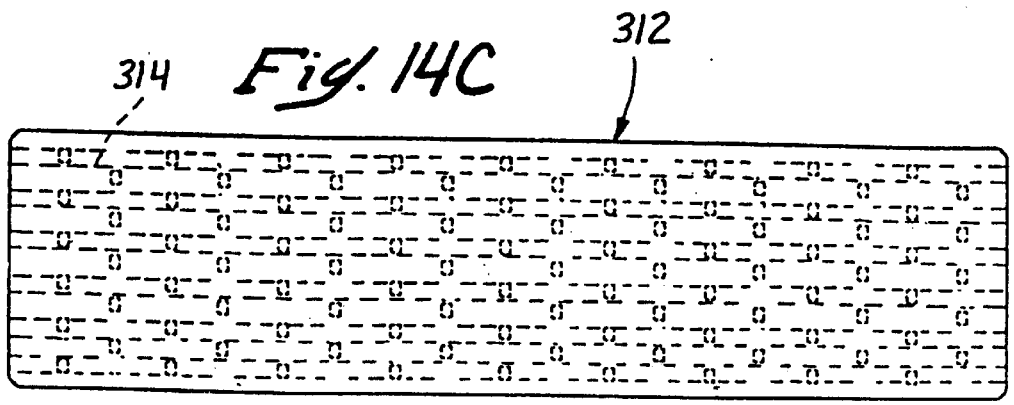

FIGS. 14A–14C illustrate three embodiments of an illuminator mat having passive cooling channels therethrough.

FIG. 14A illustrates an illuminator mat 300 having a plurality of columns of apertures 302 extending from the front side to the back side. Preferably, the columns of apertures 302 are formed in between each column of LEDs 304 for maximum heat dissipation. Of course, the apertures should avoid interference with any copper tracings or light-generating sources. FIG. 14B illustrates an illuminator 306 having a series of channels 308 extending along the width dimension. The channels 308 are desirable formed between each column 310 of the LEDs. Finally, FIG. 14C illustrate an illuminator 312 having a series of longitudinal channels 314 formed therein. Alternatively, the channels maybe formed both transversely and longitudinally for better passive cooling of the LEDs. In all of the embodiments seen in FIGS. 14A–14C, the apertures or channels are open at both ends and serve to passively dissipate heat generated by the LEDs.

Another configuration facilitating passive cooling is the use of external fins, as seen in FIGS. 15A–15C. In particular, FIG. 15A illustrates an illuminator 320 having a plurality of fins 322 extending in the width dimension. In FIG. 15C, the external fins 324 extend in the longitudinal dimension. Finally, in FIG. 15C, the fins extend both in the width and longitudinal dimensions in a waffle pattern. Also, as shown in FIG. 15A, the fins 322 are located on both the top and bottom surface of the illuminator or in between the cover and substrate. These fins provide passive cooling for the illuminators, and may be provided on the front or rear surfaces, or both. The fins can cover all or part of the illuminator, and be of different sizes to achieve a desired amount of heat transfer. The fins can be on the exterior surface of the illuminator, in a cavity, or under a covering or overwrap.

A still further variation of passive cooling is seen in the illuminator 340 of FIG. 16A. For illustration purposes, the cover 342 of the illuminator 340 is shown in phantom to reveal a plurality of pins or spacers 344 extending between the substrate 346 and cover 342. The side edges of the illuminator 340 remain open to permit passive cooling of the LEDs 348. Alternatively, the side edges may be closed and cooling medium flowed through conduit 350. In any event, the spacers 344 maintain a gap between the front cover 342 and the substrate 346 along the length of the illuminator 340.

Figure 16B:
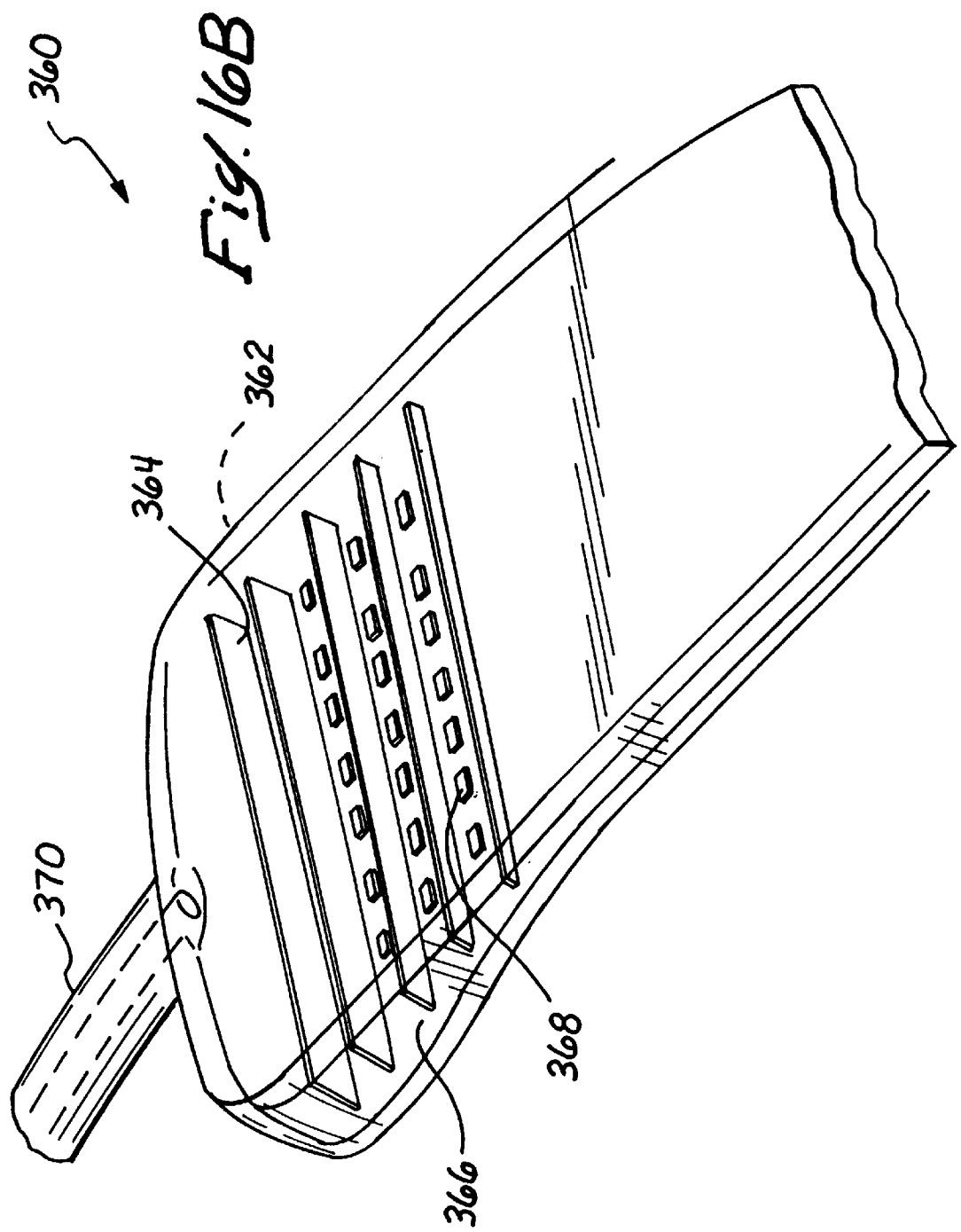
FIG. 16B is a perspective view of another alternative illuminator having internal spacer ribs.

Another variation of passive cooling is seen in the illuminator 360 of FIG. 16B. As in FIG. 16A, the cover 362 of the illuminator 360 is shown in phantom to reveal a plurality of ribs or spacers 364 extending between the substrate 366 and cover 362. The side edges of the illuminator 360 remains open to permit passive cooling of the LEDs 368. Alternatively, the side edges may be closed and cooling medium flowed through conduit 370. The ribs or spacers may be configured to channel cooling medium through the illuminator. In any event, the spacers 364 maintain a gap between the front cover 362 and the substrate 366 along the length of the illuminator 360.

Figure 17A:
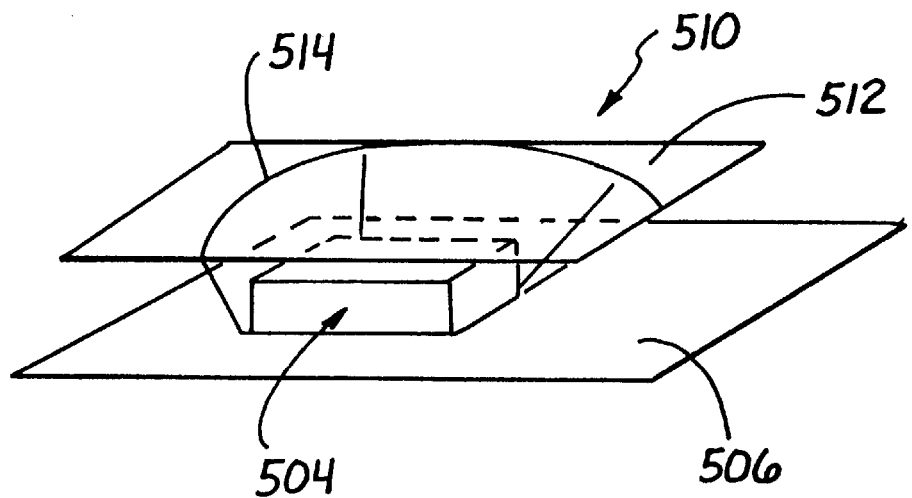
FIGS. 17A–C illustrate a still further construction of an illuminator of the present invention having a diffusive/reflective system.
Figure 17B:
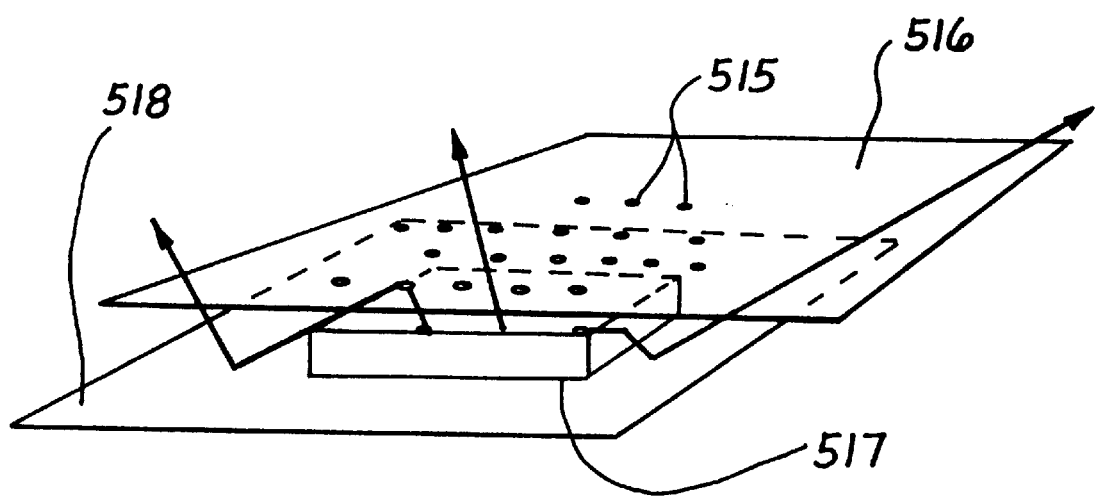
Figure 17C:
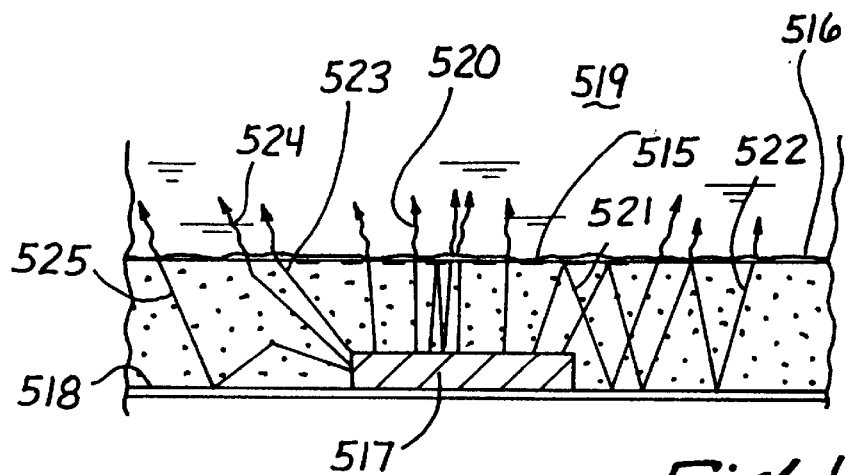

FIGS. 17A–C and 18A–D illustrate the use of paints or coatings to cause light to be diffused as desired. FIGS. 17A–C also shows how diffusion can be improved by use of a combination of diffusing elements. Reflective paints or coatings, such as coatings of titania, magnesium oxide, aluminum oxide, other white powders and the like and mixtures thereof, are useful for diffusion.

In FIG. 17A, an LED 504 is shown positioned relative to a light reflecting surface 506 of illuminator 510 in accordance with the present invention. Reflecting surface 506 can be a metallized surface or a surface with a matte finish or the like. Contact surface 512 is part of the interface of illuminator 510 and is spaced apart from LED 504. Are 514 is a representation of the intense light pattern on contact surface 512 generated by LED 504 with no light diffusion. The light within arc 514 is very intense while the light from LED 514 outside the arc is substantially less intense and may not be therapeutically effective.

FIG. 17B shows a pattern of dots 515 provided on contact surface 516 and spaced from LED 517. Again, the surface 518 on which the LED 517 is mounted is reflective. The resulting paths of reflected light are seen in FIGS. 17B and 17C. This indirect illumination helps make the emitted light more uniform on the patient's skin 519, and also redirects any light reflected from the patient back to the patient to reduce energy losses while maintaining intensity.

FIG. 17C shows a number of potential pathways for the reflected light. First, the light from the LED 517 can travel straight to the patient, as seen by arrow 520, to be absorbed into the skin 519 (absorption indicated by wiggly lines). Or, as seen by ray 521, light can strike a dot 515 and be reflected back to the reflective surface 518, to then be re-reflected back to the skin 519. Instead of passing into the skin 519, the ray 521 could be partly or wholly reflected by the patient's skin and then reflected back again to the skin by surface 518, as see at 522. Ray 523 shows light striking a roughened contact surface 516 and being deflected or bent before being absorbed into the skin 519. Ray 524 shows the light striking a particulate within the interface between the LED and contact surface 516, and then deflecting toward the skin 519. Finally, ray 525 shows light striking a particulate within the interface between the LED and contact surface 516, and then deflecting to the surface 518, to then be re-reflected back to the skin 519. This schematic representation illustrates just some of the potential light pathways, and the reader will understand that an infinite number of combinations are possible, the light ultimately being substantially absorbed by the skin 519.

Figure 18A:
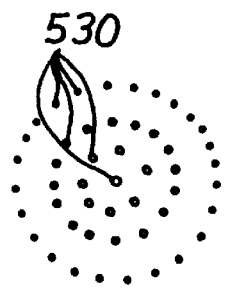
FIGS. 18A–D are schematic illustrations of various patterns useful in the construction illustrated in FIGS. 17A–C.

FIG. 18A illustrates a pattern of white dots 530 that can be painted or coated on contact surface 512 within the are 514 to diffuse the intense light. The diameter of the dots decreases from the center of the pattern outwardly. This pattern of dots 530 scatters and/or reflects some of the light back to the reflecting surface 506. The pattern of dots depends, for example, on the thickness of the layer on which the contact surface is located and its distance from LED 504, and the presence of any additional light diffusing material or materials in the interface. The pattern of dots 530 results in a substantially more diffuse, yet therapeutically effective light pattern on the contact surface 512.

Figure 18B:
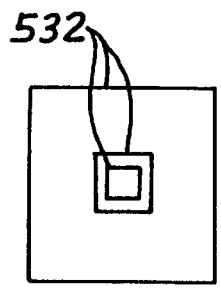
Figure 18C:
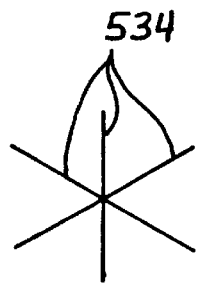
Figure 18D:
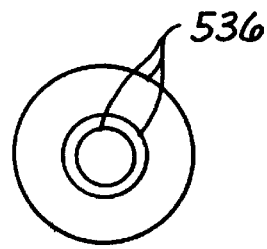

FIGS. 18B, 18C and 18D illustrate alternate coating patterns that can be used in place of dots 530. Thus, a pattern of rectangles 532, a pattern of outwardly radiating lines 534 or a series of circles 536 can be used in much the same way as dots 530 to provide for enhanced light diffusion. Any pattern may be opaque, translucent, or halftone.

While this invention has been described with respect to various specific examples and embodiments, it is to be understood that the invention is not limited thereto and that it can be variously practiced within the scope of the following claims.

What is claimed is:

1. An illuminator for delivering light energy to the skin of a patient for phototherary, the illuminator comprising:
   a thin, lightweight flexible substrate;
   a plurality of conductive traces affixed to the substrate and being adapted to connect to an electrical power source;
   at least one discrete light-generating source disposed on the substrate and coupled to the conductive traces; and
   a covering at least partly surrounding the substrate and having an exterior surface that is spaced apart from the light-generating source, the exterior surface being adapted to contact the skin of a patient, wherein the exterior surface is defined by a disposable overwrap sized to at least partly cover the illuminator and provide a contamination barrier between the illuminator and the skin of the patient.

2. The illuminator of claim 1, wherein the illuminator is structured to be placed in contact with the skin of a newborn infant and used without injury.

3. The illuminator of claim 1, which includes a plurality of discrete light-generating sources disposed on the substrate and coupled to the conductive traces.

4. The illuminator of claim 1, wherein the illuminator is configured to facilitate the transfer of heat produced by the at least one light-generating source away from the skin of the patient sufficient to prevent such heat from adversely affecting the patient.

5. The illuminator of claim 4, wherein the illuminator includes at least one fin positioned to provide increased transfer of heat produced by the light-generating sources away from the skin of the patient relative to a substantially identical illuminator without the fin.

6. The illuminator of claim 4, wherein the covering is spaced apart from the substrate and further comprising at least one cavity between the covering and the substrate.

7. The illuminator of claim 1, further including a reflector for reflecting light from the at least one light-generating source toward the patient, wherein the light-generating source comprises an LED, and the reflector comprises a thin, flexible sheet.

8. The illuminator of claim 1, further including cooling means for transferring heat generated by the at least one light-generating source so that the illuminator can safely and comfortably contact the skin of a patient.

9. The illuminator of claim 1, further including diffusing means for diffusing light emitted from the at least one light-generating source.

10. An illuminator for delivering light energy to the skin of a patient for phototherapy, the illuminator comprising:
    a thin, lightweight substrate;
    a plurality of conductive traces affixed to the substrate and being adapted to connect to an electrical power source;
    at least one light-generating source disposed on the substrate and coupled to the conductive traces;
    an interface at least partly covering the light-generating source on the substrate, the interface providing heat transfer means to transfer heat generated by the light-generating source so that an external surface of the illuminator can safely contact the skin of a patient, wherein the interface defines spaces between the external surface and the substrate; and
    at least one fin positioned to provide increased transfer of heat produced by the light-generating sources away from the skin of the patient relative to a substantially identical illuminator without the fin.

11. The illuminator of claim 10, wherein the illuminator is flexible and adapted to conform to the skin of the patient.

12. The illuminator of claim 10, wherein the interface comprises a thermal insulating layer.

13. The illuminator of claim 10, wherein the illuminator defines a skin-contacting surface and has an average intensity in excess of about 50 microwatts per square centimeter at the skin-contacting surface, and the maximum temperature of the skin-contacting surface is limited to about 110° F. or less.

14. The illuminator of claim 10, wherein the interface comprises a flexible, polymeric layer permitting light energy to penetrate therethrough and conforming to the skin of a patient.

15. An illuminator for delivering light energy to the skin of a patient for phototherapy, the illuminator comprising:
    a thin, lightweight substrate;
    a plurality of conductive traces affixed to the substrate and being adapted to connect to an electrical power source;
    at least one light-generating source disposed on the substrate and coupled to the conductive traces;
    an interface at least partly covering the light-generating source on the substrate, the interface providing heat transfer means to transfer heat generated by the light-generating source so that an external surface of the illuminator can safely contact the skin of a patient wherein the interface defines spaces between the external surface and the substrate; and
    wherein the spaces comprise channels for convective heat transfer, and further including means for actively cooling the at least one light-generating source using the channels.

16. An illuminator for delivering light energy to the skin of a patient for phototherary, the illuminator comprising:
- a thin, lightweight substrate;
- a plurality of conductive traces affixed to the substrate and being adapted to connect to an electrical power source;
- at least one light-generating source disposed on the substrate and coupled to the conductive traces;
- an interface at least partly covering the light-generating source on the substrate, the interface providing heat transfer means to transfer heat generated by the light-generating source so that an external surface of the illuminator can safely contact the skin of a patient, wherein the interface defines spaces between the external surface and the substrate; and
- wherein there are a plurality of the light-generating sources, and the spaces are adjacent to the light-generating sources.

17. An illuminator for delivering light energy to the skin of a patient for phototherary, the illuminator comprising:
- a thin, lightweight substrate;
- a plurality of conductive traces affixed to the substrate and being adapted to connect to an electrical power source;
- at least one light-generating source disposed on the substrate and coupled to the conductive traces;
- an interface at least partly covering the light-generating source on the substrate, the interface providing heat transfer means to transfer heat generated by the light-generating source so that an external surface of the illuminator can safely contact the skin of a patient, wherein the interface defines spaces between the external surface and the substrate; and
- wherein the spaces are in communication with apertures provided through the external surface of the illuminator.

18. An illuminator for delivering light energy to the skin of a patient for phototherary, the illuminator comprising:
- a thin, lightweight substrate;
- a plurality of conductive traces affixed to the substrate and being adapted to connect to an electrical power source;
- at least one light-generating source disposed on the substrate and coupled to the conductive traces;
- an interface at least partly covering the light-generating source on the substrate, the interface providing heat transfer means to transfer heat generated by the light-generating source so that an external surface of the illuminator can safely contact the skin of a patient, wherein the interface defines spaces between the external surface and the substrate; and
- diffusing means for diffusing light emitted from the at least one light-generating source.

19. An illuminator for delivering light energy to the skin for phototherapy, the illuminator comprising:
- a thin, lightweight substrate;
- a plurality of conductive traces affixed to the substrate and being adapted to connect to an electrical power source;
- at least one discrete light-generating source disposed on the substrate and coupled to the conductive traces; and
- an interface at least partly covering the light-generating source on the substrate, the interface diffusing the light emitted from the discrete light-generating source, the illuminator being adapted to contact the skin of a patient, wherein the interface comprises a combination of at least two materials having different refractive indices.

20. The illuminator of claim 19, wherein the interface comprises at least one material to diffuse light emitted from the at least one discrete light-generating source.

21. The illuminator of claim 19, wherein the interface has an exterior surface adapted to contact the skin of a patient, the exterior surface having surface deformities to diffuse the light emitted from the at least one discrete light-generating source.

22. The illuminator of claim 19, wherein the at least one discrete light-generating source is an LED.

23. The illuminator of claim 19, further including a reflector for reflecting light from the at least one discrete light-generating source toward the patient.

24. A wearable photo therapeutic illuminator for delivering light energy to the skin of a patient, comprising:
- a flexible substrate;
- a plurality of light-generating sources disposed on the substrate; and
- a flexible, polymeric layer covering the light-generating sources, the layer permitting light energy to penetrate therethrough and adapted to substantially conform to the skin of a patient, the layer comprising a matrix with glass bubbles dispersed therein to diffuse the light emitted from the light-generating sources.

25. The illuminator of claim 24, further including cooling means for transferring heat generated by the at least one light-generating source so that the illuminator can safely and comfortably contact the skin of a patient.

26. The illuminator of claim 24, wherein there are a plurality of the light-generating sources, the layer having an exterior surface adapted to contact the skin of the patient, the exterior surface being uneven to diffuse the light emitted from the light-generating sources.

27. The illuminator of claim 24, wherein the illuminator further includes a diffusive reflector to reflect light emitted from the light-generating sources in a diffusive manner toward the skin of the patient.

28. An illuminator for delivering light energy to the skin of a patient for phototherary, the illuminator comprising:
- at least one discrete light-generating source disposed on one side of a substrate and facing the skin of the patient;
- a diffusive reflector on the substrate and positioned to reflect light emitted from the light-generating source in a diffusive manner toward the skin of the patient; and
- an exterior surface adapted to contact the skin of a patient.

29. The illuminator of claim 28 wherein the diffusive reflector has a Lambertian reflecting surface.

30. The illuminator of claim 28 further comprising an additional diffusing means to direct at least a portion of the light emitted by the at least one light-generating source away from a location on the patient where it would have gone but for such means, and towards the diffusive reflector.

31. A method of phototherary, comprising:
- providing a flexible illuminator comprising at least one discrete light-generating source and a covering at least partly surrounding the light-generating source, the covering having an exterior surface that is spaced apart from the light-generating source and adapted to contact the skin of a patient;
- interposing a disposable wrap between the exterior surface and the patient;
- applying the flexible illuminator to the skin of a patient having a disorder; and
- emitting light from the light-generating source sufficient for therapeutic treatment of the disorder.

32. The method of claim 31, further including:
diffusing light emitted from the light-generating source.

33. The method of claim 31, further including:
transferring heat generated by the light generating source away from the skin of the patient.

34. The method of claim 31, wherein the disorder is selected from the group consisting of:
bulimia nervosa;
herpes;
psoriasis;
seasonal affective disorder;
sleep disorders;
acne;
skin cancer; and
hyperbilirubinemia.

35. A method of phototherary, comprising:
providing an illuminator comprising at least one discrete light-generating source disposed on one side of a substrate and facing the skin of the patient and a diffusive reflector, the illuminator having an exterior surface adapted to contact the skin of a patient, the diffusive reflector on the substrate and positioned to reflect light emitted from the light generating source in a diffusive manner toward the skin of the patient;
applying the illuminator to the skin of a patient having a disorder; and
providing light from the light-generating source sufficient for therapeutic treatment of the disorder.

36. The method of claim 35, wherein the illuminator further comprises an additional diffusing means to direct at least a portion of the light emitted by the at least one light-generating source away from a location on the patient where it would have gone but for such means, and toward the diffusive reflector.

37. The method of claim 35, wherein the disorder is selected from the group consisting of:
bulimia nervosa;
herpes;
psoriasis;
seasonal affective disorder;
sleep disorders;
acne;
skin cancer; and
hyperbilirubinemia.

38. A method of phototherary, comprising:
providing an illuminator comprising at least one discrete light-generating source on a substrate and an interface at least partly covering the light-generating source on the substrate, the interface providing internal channels to transfer heat generated by the light-generating source so that the illuminator is cooled and can safely contact the skin of a patient;
applying the illuminator to the skin of a patient having a disorder; and
providing light from the light-generating source sufficient for therapeutic treatment of the disorder.

39. The method of claim 38, wherein the illuminator further comprising a diffusive reflector positioned to diffuse light emitted from the light generating source.

40. The method of claim 38, wherein the disorder is selected from the group consisting of:
bulimia nervosa;
herpes;
psoriasis;
seasonal affective disorder;
sleep disorders;
acne;
skin cancer; and
hyperbilirubinemia.

41. A wearable photo therapeutic illuminator for delivering the light energy to the skin of a patient, comprising:
a flexible substrate;
a plurality of light-generating sources disposed on the substrate; and
a flexible, polymeric layer covering the light-generating sources, the layer permitting light energy to penetrate therethrough and adapted to substantially conform to the skin of a patient, the layer comprising a matrix with titania dispersed therein to diffuse the light emitted from the light-generating sources.

42. A wearable phototherapeutic illuminator for delivering light energy to the skin of a patient, comprising:
a flexible substrate;
a plurality of light-generating sources disposed on the substrate; and
a flexible, polymeric layer covering the light-generating sources, the layer permitting light energy to penetrate the therethrough and adapted to substantially conform to the skin of a patient, the layer comprising a blend of at least two materials having different refractive indexes to diffuse the light emitted from the light-generating sources.

43. An illuminator for delivering light energy to the skin for phototherary, the illuminator comprising:
a thin, lightweight substrate;
a plurality of conductive traces affixed to the substrate and being adapted to connect to an electrical power source;
a plurality of discrete light-generating sources disposed on the substrate and coupled to the conductive traces; and
an interface covering the substrate and the light-generating sources thereon, the interface having a diffusive layer that diffuses the discrete points of light emitted from the sources to result in a more uniform overall emittance, the illuminator being adapted to contact the skin of a patient.

44. The illuminator of claim 43, wherein the diffusive layer comprises a combination of at least two materials having different refractive indexes.

45. The illuminator of claim 43, wherein the interface has an exterior surface adapted to contact the skin of a patient, the exterior surface having surface deformities defining the diffusive layer.

46. The illuminator of claim 43, wherein the diffusive layer comprises a matrix with glass bubbles dispersed therein.

47. The illuminator of claim 43, wherein the diffusive layer comprises a matrix with titania dispersed therein.

48. The illuminator of claim 43, further including cooling means for transferring heat generated by the light-generating sources so that the illuminator can safely and comfortably contact the skin of a patient.

49. An illuminator for delivering light energy to the skin of a patient for phototherary, the illuminator comprising:
a thin, lightweight substrate;
a plurality of conductive traces affixed to the substrate and being adapted to connect to an electrical power source;

at least one light-generating source disposed on the substrate and coupled to the conductive traces;

an interface at least partly covering the light-generating source on the substrate, the interface providing heat transfer means to transfer heat generated by the light-generating source so that an external surface of the illuminator can safely contact the skin of a patient, wherein the interface defines spaces between the external surface and the substrate; and wherein the interface includes a generally planar member defining on a side facing the substrate a plurality of spacers positioned between the planar member and the substrate to create the spaces, the spaces being in fluid communication to permit cooling of the light-generating source.

50. The illuminator of claim 49, wherein the spacers are pins.

51. The illuminator of claim 49, wherein the spacers are fins.

52. The illuminator of claim 49, wherein the spacers are vanes.

53. The illuminator of claim 49, wherein the spacers are ridges.

54. The illuminator of claim 49, wherein the spacers are ribs.

* * * * *

UNITED STATES PATENT AND TRADEMARK OFFICE
CERTIFICATE OF CORRECTION

PATENT NO.    : 6,290,713 B1
DATED         : September 18, 2001
INVENTOR(S)   : Russell It is certified that error appears in the above-identified patent and that said Letters Patent is hereby corrected as shown below:

<u>Title page,</u>
Item [57], ABSTRACT,
Line 5, "source" should be -- sources --.

<u>Column 1,</u>
Line 29, after "bilirubin is" delete "a".

<u>Column 2,</u>
Line 2, after "spaced" insert -- apart --.

<u>Column 3,</u>
Line 27, "safely effective" should be -- safely and effectively --.

<u>Column 4,</u>
Line 10, "characteristic" should be -- characteristics --.

<u>Column 7,</u>
Line 42, "application" should be -- applications --.

<u>Column 8,</u>
Line 14, "Substrate" should be -- Substrates --.
Line 28, "thickness" should be -- thicknesses --.
Line 41, "adhesive" should be -- adhesives --.

<u>Column 10,</u>
Line 5, "illumination" should be -- illuminator --.
Line 39, "index or" should be -- illuminator --.
Line 41, "of reflectors" should be -- or reflectors --.
Line 66, "embodiment" should be -- embodiments --.

<u>Column 12,</u>
Line 17, "variety shapes" should be -- variety of shapes --.
Line 31, "affected" should be -- affect --.

<u>Column 13,</u>
Line 19, "characteristic" should be -- characteristics --.

<u>Column 14,</u>
Line 18, "other(e.g.," should be -- other (e.g., --.
Line 23, "metals(e.g.," should be -- metals (e.g., --.

UNITED STATES PATENT AND TRADEMARK OFFICE
CERTIFICATE OF CORRECTION

PATENT NO. : 6,290,713 B1
DATED : September 18, 2001
INVENTOR(S) : Russell

It is certified that error appears in the above-identified patent and that said Letters Patent is hereby corrected as shown below:

Column 16
Line 16, after "include" delete "a".
Line 47, "illustrate" should be -- illustrates --.

Column 17,
Line 51, "desirable formed" should be -- desirably formed --.
Line 54, "maybe" should be -- may be --.

Column 18,
Line 23, "remain" should be -- remains --.
Line 43, "Are" should be -- Arc --.
Line 67, "as see" should be -- as seen --.

Column 19,
Line 14, "are" should be -- arc --
Line 38, "phototherary" should be -- phototherapy --.

Column 21,
Lines 2, 20 and 37, "phototherary" should be -- phototherapy --.

Column 22,
Line 14, "photo therapeutic" should be -- phototherapeutic --.
Line 33, delete "being uneven" and insert -- having surface deformities --.
Lines 39, and 54, "phototherary" should be -- phototherapy --.
Line 48, after "Lambertain" insert -- (random) --.

Column 23,
Line 16, "phototherary" should be -- phototherapy --.

Column 24,
Line 8, "photo therapeutic" should be -- phototherapeutic --.
Line 27, before "therethrough" delete "the".

UNITED STATES PATENT AND TRADEMARK OFFICE
CERTIFICATE OF CORRECTION

PATENT NO. : 6,290,713 B1
DATED : September 18, 2001
INVENTOR(S) : Russell

It is certified that error appears in the above-identified patent and that said Letters Patent is hereby corrected as shown below:

Column 24 (cont'd),
Lines 33 and 64, "phototherary" should be -- phototherapy --.

Signed and Sealed this

Seventh Day of September, 2004

JON W. DUDAS
*Director of the United States Patent and Trademark Office*